United States Patent
Srinivasan et al.

(10) Patent No.: US 10,980,936 B2
(45) Date of Patent: Apr. 20, 2021

(54) PEN NEEDLE MAGAZINE

(71) Applicant: Becton, Dickinson and Company, Franklin Lakes, NJ (US)

(72) Inventors: Sudarsan Srinivasan, North Brunswick, NJ (US); Cole Constantineau, Cambridge, MA (US); Michel Bruehwiler, Newton, MA (US); Tyson Montidoro, Davie, FL (US); Jeffrey Chagnon, Somerville, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 359 days.

(21) Appl. No.: 16/095,774

(22) PCT Filed: Mar. 31, 2017

(86) PCT No.: PCT/US2017/025500
§ 371 (c)(1),
(2) Date: Oct. 23, 2018

(87) PCT Pub. No.: WO2017/189174
PCT Pub. Date: Nov. 2, 2017

(65) Prior Publication Data
US 2019/0125958 A1 May 2, 2019

Related U.S. Application Data

(60) Provisional application No. 62/328,688, filed on Apr. 28, 2016.

(51) Int. Cl.
*A61M 5/00* (2006.01)
*A61M 5/32* (2006.01)
(Continued)

(52) U.S. Cl.
CPC .......... *A61M 5/002* (2013.01); *A61M 5/3202* (2013.01); *A61M 5/3293* (2013.01);
(Continued)

(58) Field of Classification Search
CPC .. A61M 5/002; A61M 5/3202; A61M 5/3293; A61M 5/3297; A61M 2005/004;
(Continued)

(56) References Cited

U.S. PATENT DOCUMENTS

| | | |
|---|---|---|
| 5,829,589 A | 11/1998 | Nguyen et al. |
| 5,873,462 A | 2/1999 | Nguyen et al. |

(Continued)

FOREIGN PATENT DOCUMENTS

| | | |
|---|---|---|
| EP | 2119423 A1 | 11/2009 |
| EP | 2420270 A2 | 2/2012 |

(Continued)

OTHER PUBLICATIONS

Li-Yuan Chang et al., "Integrated Flow Sensing for Focal Biochemical Stimulation", Proceedings of the Third IEEE International Conference on Nano/Micro Engineered and Molecular Systems, Jan. 6-9, 2008, Sanya, China, pp. 921-926, (6 Pages Total).

*Primary Examiner* — Bhisma Mehta
*Assistant Examiner* — John J Crawford
(74) *Attorney, Agent, or Firm* — Dickinson Wright PLLC

(57) ABSTRACT

An attachable needle assembly (102) for use on a medication delivery pen (104), the needle assembly (102) comprising a housing (1 10) enclosing a hub (106) having a communication needle (108) configured to engage the medication delivery pen (104) and pierce a reservoir septum of the medication delivery pen (104), a communication septum (172, 176) of the needle assembly (102) defining a septum chamber (180, 182) that is in fluid communication with the communication needle (108), a plurality of needles (118)

(Continued)

disposed in the communication septum (172, 176), a follower ring (130) that determines which needle (124) of the plurality of needles (118) is to be selected, and a snap ring (136) that exposes the selected needle (124) and moves the selected needle (124) in fluid communication with the septum chamber (180, 182), wherein when the housing (110) is in a first position, the plurality of needles (118) is not exposed, and when the housing (110) is in a second position, the selected needle (124) is in fluid communication with the septum chamber (180, 182) and exposed for medicament delivery.

33 Claims, 23 Drawing Sheets

(51) Int. Cl.
*A61M 5/34* (2006.01)
*A61M 5/28* (2006.01)

(52) U.S. Cl.
CPC ........ *A61M 5/3297* (2013.01); *A61M 5/3298* (2013.01); *A61M 5/345* (2013.01); *A61M 5/288* (2013.01); *A61M 2005/004* (2013.01); *A61M 2205/582* (2013.01); *A61M 2205/583* (2013.01); *A61M 2205/584* (2013.01)

(58) Field of Classification Search
CPC . A61M 2205/582; A61M 5/345; A61M 5/288
See application file for complete search history.

(56) References Cited

U.S. PATENT DOCUMENTS

| | | | |
|---|---|---|---|
| 5,931,817 | A | 8/1999 | Nguyen et al. |
| 8,876,780 | B2 | 11/2014 | Bruehwiler et al. |
| 9,101,724 | B2 | 8/2015 | Chapin et al. |
| 9,107,988 | B2 | 8/2015 | Bruehwiler et al. |
| 9,155,838 | B2 | 10/2015 | Bilton et al. |
| 9,381,303 | B2 | 7/2016 | Abhijitsinh et al. |
| 9,717,860 | B2 | 8/2017 | Bruehwiler et al. |
| 10,029,042 | B2 | 7/2018 | Searle et al. |
| 2001/0014792 | A1 | 8/2001 | West et al. |
| 2002/0020646 | A1 | 2/2002 | Groth et al. |
| 2002/0020647 | A1 | 2/2002 | Groth |
| 2005/0084631 | A1 | 4/2005 | Anderson |
| 2008/0312604 | A1 | 12/2008 | Boesen |
| 2010/0217206 | A1 | 8/2010 | Lum et al. |
| 2011/0068034 | A1 | 3/2011 | Hwang et al. |
| 2012/0004620 | A1 | 1/2012 | Spool et al. |
| 2012/0016315 | A1 | 1/2012 | Radmer et al. |
| 2012/0041373 | A1* | 2/2012 | Bruehwiler ......... A61M 5/3243 604/173 |
| 2012/0041381 | A1 | 2/2012 | Raj et al. |
| 2012/0041383 | A1 | 2/2012 | Bruehwiler et al. |
| 2012/0041390 | A1 | 2/2012 | Spool et al. |
| 2013/0041321 | A1* | 2/2013 | Cross ................. A61M 5/2448 604/189 |
| 2013/0053751 | A1 | 2/2013 | Holtham |
| 2014/0076758 | A1 | 3/2014 | Dasbach et al. |
| 2014/0123479 | A1 | 5/2014 | Dasbach |
| 2014/0262884 | A1 | 9/2014 | Priebe et al. |
| 2014/0299622 | A1 | 10/2014 | Hofmann et al. |
| 2014/0332425 | A1 | 11/2014 | Hofmann et al. |
| 2014/0339113 | A1 | 11/2014 | Hofmann et al. |
| 2015/0025469 | A1 | 1/2015 | Larsen et al. |
| 2015/0163898 | A1 | 6/2015 | Mokhtarzad |
| 2015/0283333 | A1 | 10/2015 | Butler et al. |
| 2015/0335827 | A1 | 11/2015 | Stefansen et al. |
| 2015/0346184 | A1 | 12/2015 | Galasso |
| 2016/0000992 | A1 | 1/2016 | Steel et al. |
| 2016/0030683 | A1 | 2/2016 | Taylor et al. |
| 2016/0074587 | A1 | 3/2016 | Searle et al. |
| 2016/0082195 | A1 | 3/2016 | Atterbury et al. |
| 2016/0106925 | A1 | 4/2016 | Boesen |

FOREIGN PATENT DOCUMENTS

| | | |
|---|---|---|
| EP | 2428236 A1 | 3/2012 |
| EP | 2586475 A1 | 5/2013 |
| EP | 2604304 A1 | 6/2013 |
| EP | 2696913 B1 | 9/2015 |
| WO | 2008/150715 A1 | 12/2008 |
| WO | WO-2011083055 A1 | 7/2011 |
| WO | 2014/020001 A1 | 2/2014 |
| WO | 2016/050902 A1 | 4/2016 |

* cited by examiner

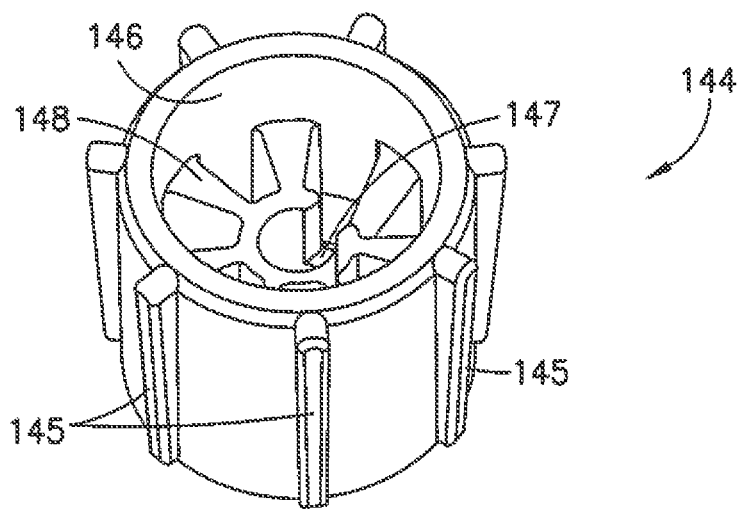
FIG.22
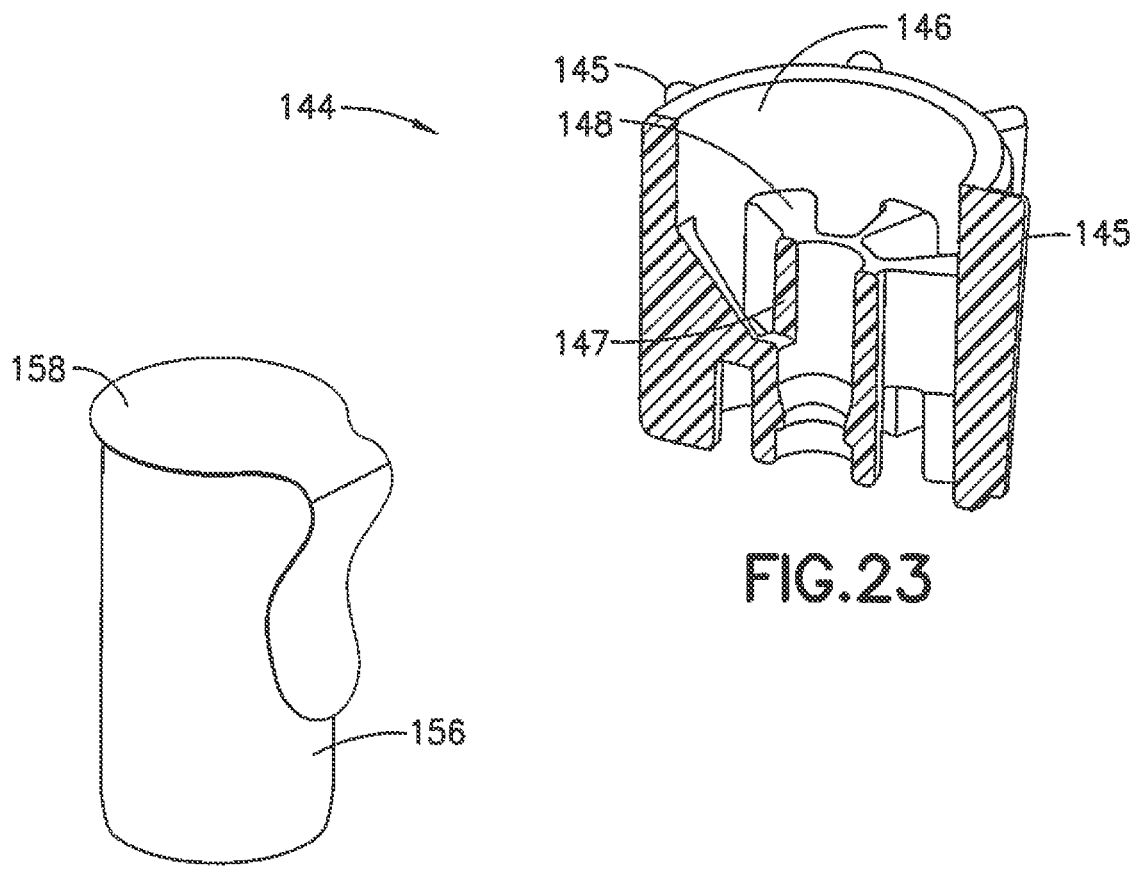
FIG.23
FIG.24

PEN NEEDLE MAGAZINE

This application claims the benefit under 35 U.S.C. § 119(e) of U.S. Provisional Patent Application Ser. 62/328,688, filed on Apr. 28, 2016, which is hereby incorporated by reference in its entirety.

FIELD

Various exemplary embodiments of the invention relate to medication pens.

BACKGROUND

Medication pens are typically used to inject medication into a patient. A person who must periodically self-inject doses of medication will typically carry a medication pen and several single-use pen needles. A medication pen is designed for safety and sterility. However, inefficiencies and inconveniences arise.

SUMMARY OF THE INVENTION

It is an aspect of the present invention to provide a needle assembly that is attachable to a medication pen to provide a magazine of needles for use. Such a needle assembly provides advantages in separating a patient end and a non-patient end and allows for engagement and disengagement. Moreover, improvements in sterility and simplicity are achieved by the needle assembly such that none of the needles in the magazine are piercing the septum of the medication pen at any point during operation, each needle is used for injection one at a time, and each needle only moves axially.

Having a magazine of needles available for medication delivery reduces needle reuse. Needle reuse is undesired for at least the following reasons. The needle dulls after a single use and so subsequent use may cause pain to the patient. Multiple needle use can also reduce the strength of the needle tip which may cause a potential fracture. Also, needle reuse increases sanitary concerns and health risks to the patient.

The needle assembly of the present invention advantageously reduces reuse for at least the following reasons. Although patients may desire to financially benefit from using a needle multiple times, the needle assembly is configured to prevent each of the plurality of needles from being used more than once. Convenience is another reason patients reuse needles. Patients may also be concerned with not having another needle available for use or not having access to supplies. However, the needle assembly conveniently provides multiple needles so that an unused needle is more readily available.

The foregoing and/or other aspects of the present invention can be achieved by providing an attachable needle assembly for use on a medication delivery pen, the needle assembly comprising a housing enclosing a hub fixed to a communication needle, the hub being configured to engage the medication delivery pen and the communication needle being configured to pierce a reservoir septum of the medication delivery pen, a communication septum of the needle assembly defining a septum chamber, the septum chamber of the needle assembly being in continuous fluid communication with the communication needle, a plurality of needles disposed in the communication septum of the needle assembly, a follower ring that rotates and identifies which needle of the plurality of needles is to be selected, and a snap ring that applies a force to expose the selected needle and moves the selected needle to be in fluid communication with the septum chamber of the communication septum of the needle assembly, wherein when the housing is in a first position, the plurality of needles is not exposed, and when the housing is in a second position, the selected needle of the plurality of needles is in fluid communication with the septum chamber of the communication septum of the needle assembly and exposed for medicament delivery.

The foregoing and/or other aspects of the present invention can also be achieved by a method of operating an attachable needle assembly for a medication delivery pen, the method comprising piercing a reservoir septum of the medication delivery pen with a communication needle, the communication needle enclosed in a hub of a housing, connecting the medication delivery pen to the hub, establishing fluid communication between the communication needle and a septum chamber of a communication septum of the needle assembly, disposing a plurality of needles in the communication septum of the needle assembly, rotating a portion of the needle assembly to identify which needle of the plurality of needles is to be selected, and applying a force to the selected needle to expose the selected needle and to move the selected needle to be in fluid communication with the septum chamber of the communication septum of the needle assembly, wherein when the housing is in a first position, the plurality of needles is not exposed, and when the housing is in a second position, the selected needle of the plurality of needles is in fluid communication with the septum chamber of the communication septum of the needle assembly and is exposed for medicament delivery.

Additional and/or other aspects and advantages of the present invention will be set forth in the description that follows, or will be apparent from the description, or may be learned by practice of the invention.

BRIEF DESCRIPTION OF THE DRAWINGS

The above aspects and features of the present invention will be more apparent from the description for the exemplary embodiments of the present invention taken with reference to the accompanying drawings, in which:

FIG. 22 illustrates a perspective view of a bottom guide;

FIG. 23 illustrates a cross sectional perspective view of the bottom guide;

FIG. 24 illustrates a perspective view of the needle assembly in the cover and sealed by a teardrop label;

DETAILED DESCRIPTION OF EXEMPLARY EMBODIMENTS

Figure 2:
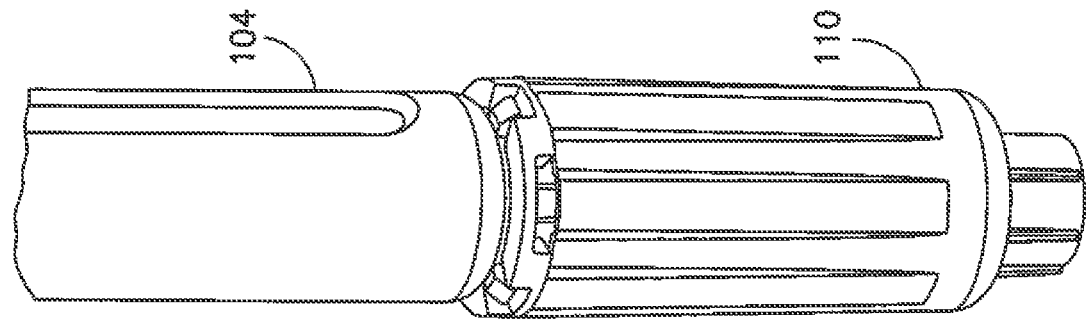
FIG. 2 illustrates a perspective view of the needle assembly attached to the medication delivery pen with a cover removed.
Figure 1:
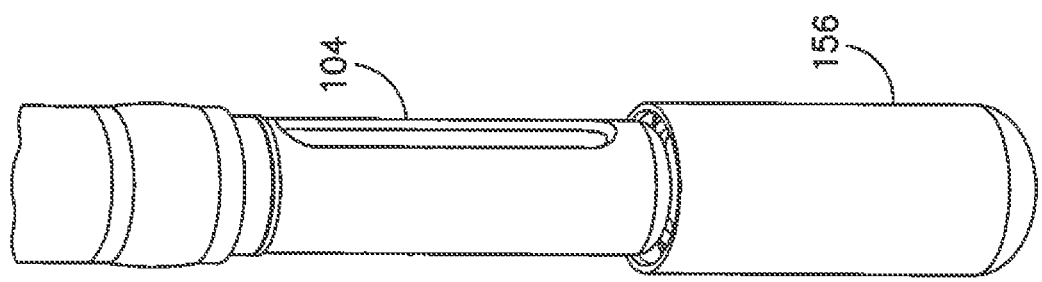
FIG. 1 illustrates a perspective view of an exemplary needle assembly attached to a medication delivery pen.

FIG. 1 illustrates a typical medication delivery pen 104 used for injecting medicament, such as liquid drugs, into a living body. A needle assembly 102 is mounted on the medication delivery pen 104 to enhance medication delivery. The needle assembly 102 is enclosed in a cover 156 prior to use. FIG. 2 illustrates the needle assembly 102 with the cover 156 removed, exposing a housing 110. Benefits and advantages of the needle assembly 102 are described below.

Figure 12:
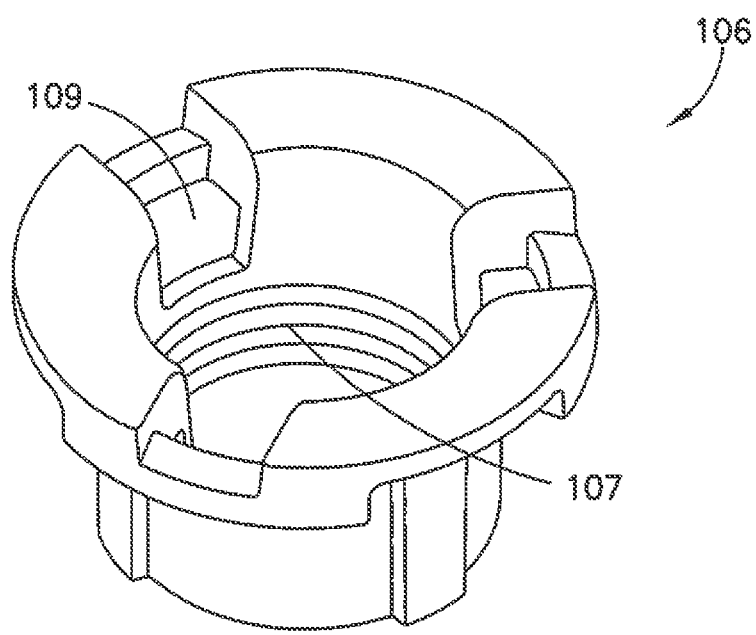
FIG. 12 illustrates a perspective view of a hub.

According to one embodiment, FIGS. 3-8 illustrate the needle assembly 102 mounted on the medication delivery pen 104 in a first position. The needle assembly 102 includes a hub 106. FIG. 12 illustrates the hub 106 having internal threads 107 that engage external threads (not shown) of the medication delivery pen 104. The threaded assembly allows a user to attach and detach the needle assembly 102 from the medication delivery pen 104. Although threads are disclosed, a variety of engagement mechanisms are contemplated, such as a press-fit, laser welding or the use of adhesives.

FIG. 12 also illustrates the hub 106 including a plurality of hub mounting holes 109. The plurality of hub mounting holes 109 engages a septum housing 114 of the needle assembly 102. The plurality of hub mounting holes 109 includes three although more or less is contemplated.

The hub 106 encloses a hollow communication needle 108 that is configured to pierce a vial, cartridge or reservoir septum (not shown) of the medication delivery pen 104. The communication needle 108 is fixed to the hub 106 at a hub mount 105 via a press-fit, laser welding or the use of adhesives, for example. The hub mount 105 also engages the hub 106 to a communication septum 172, 176.

When the needle assembly 102 is mounted on the medication delivery pen 104, a sharpened proximal end of the communication needle 108 pierces the reservoir septum (not shown) to establish fluid communication between the needle assembly 102 and the medication delivery pen 104. Specifically, the communication needle 108 piercing the reservoir septum provides fluid communication between the needle assembly 102 and an insulin cartridge, for example, of the medication delivery pen 104.

Figure 13:
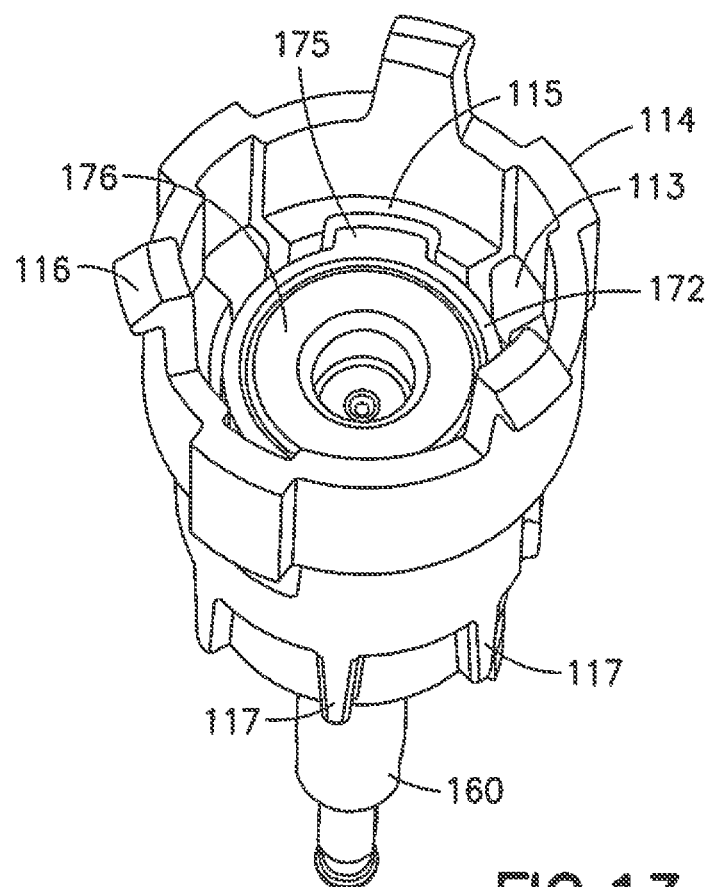
FIG. 13 illustrates a perspective view of a septum housing.

According to one embodiment, the septum housing 114 includes a plurality of openings 113, an alignment notch 115, a plurality of septum housing flanges 116 and a plurality of external ridges 117. The plurality of openings 113 includes, preferably, three openings. The plurality of openings 113 are configured to engage a tactile ring 190 as described in detail below. The alignment notch 115, as illustrated in FIG. 13, aids in assembly for aligning the septum housing 114 to the communication septum 172, 176. The plurality of septum housing flanges 116 engages the plurality of hub mounting holes 109 to secure these two parts together. The plurality of external ridges 117 provides a means to rotate a plurality of hollow needles 118 for use in the needle assembly 102.

Figure 3:
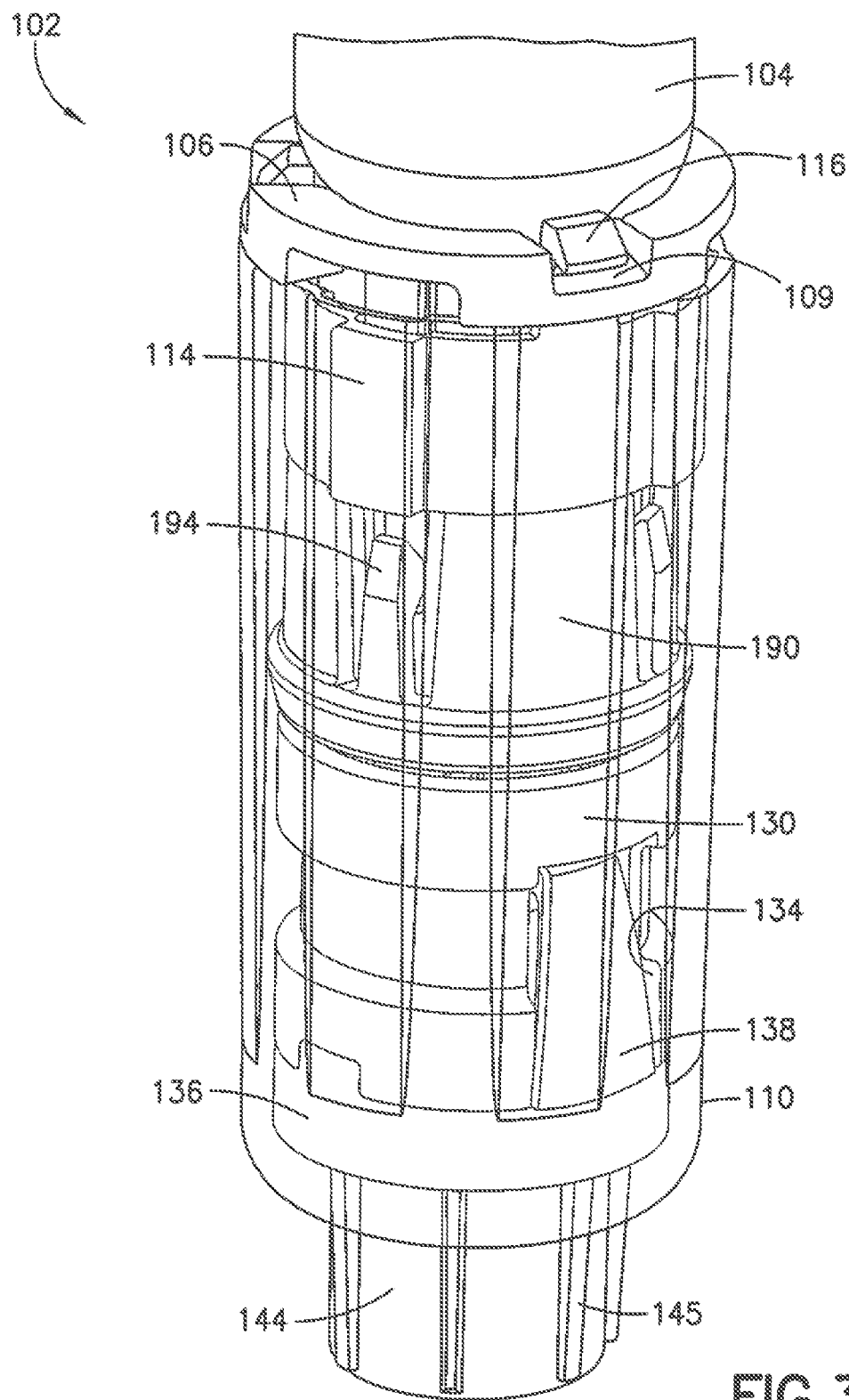
FIG. 3 illustrates a front elevation view of the needle assembly in a first position with a transparent housing for ease of illustration.
Figure 5:
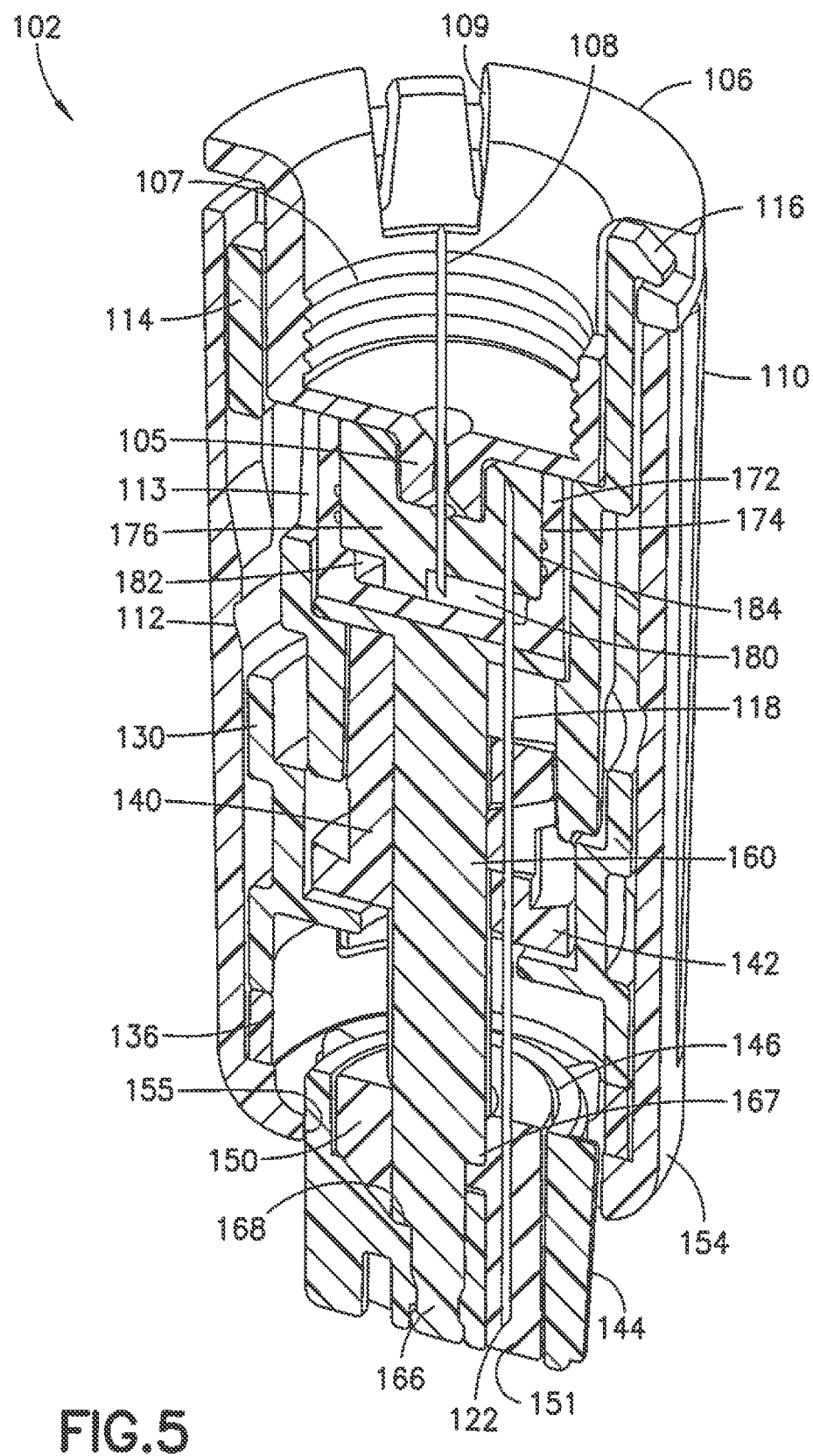
FIG. 5 illustrates a cross sectional view of the needle assembly in the first position.
Figure 7:
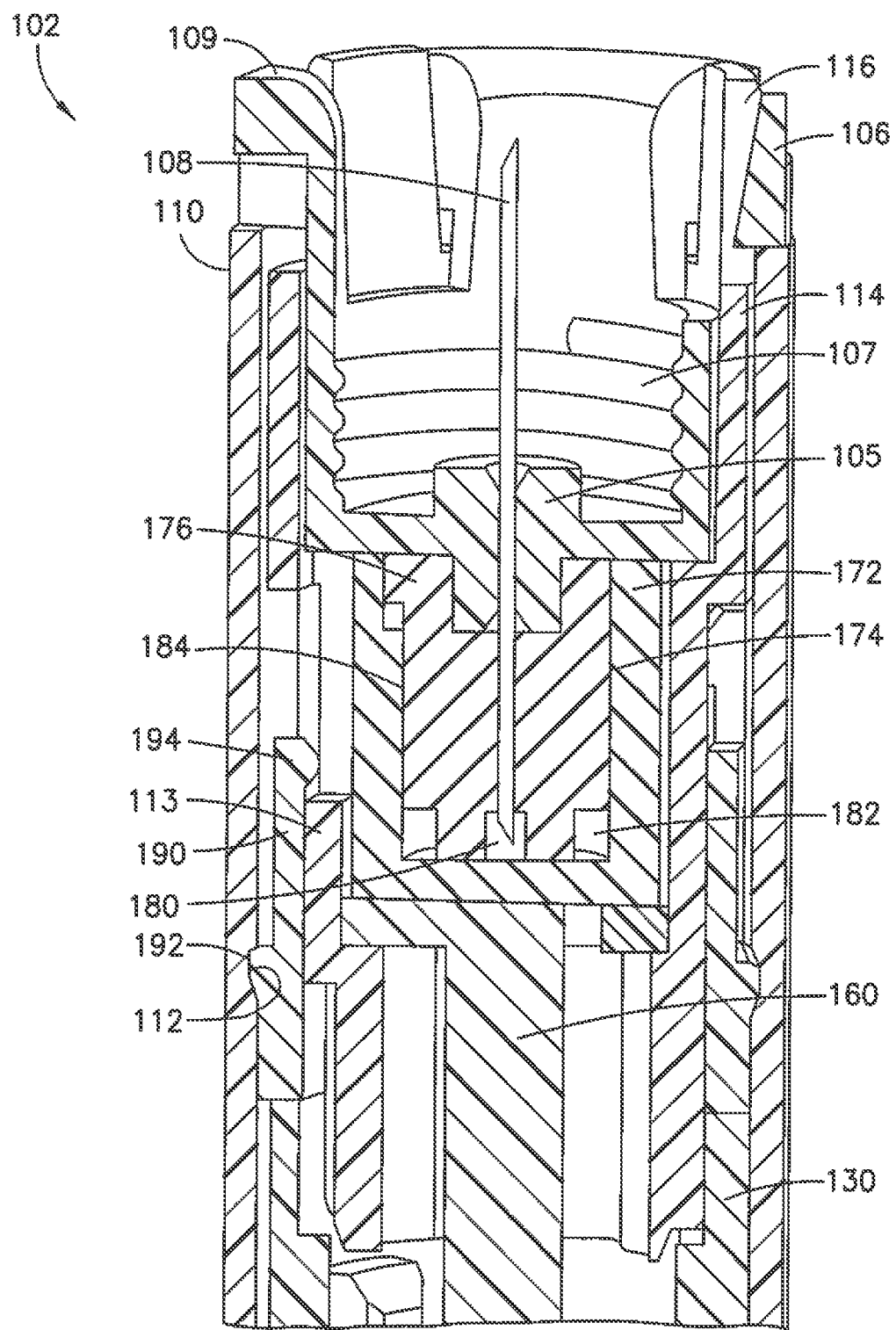
FIG. 7 illustrates a cross sectional view of the needle assembly including a tactile ring in the first position.
Figure 20:
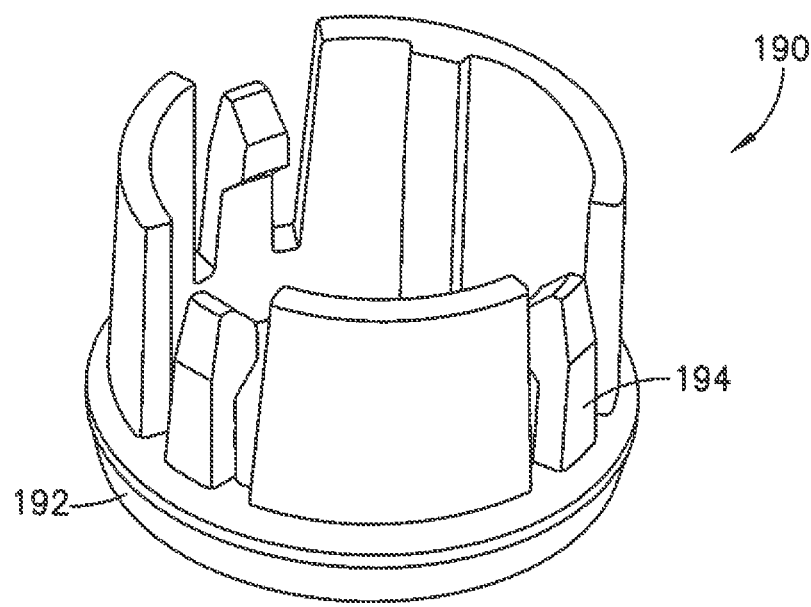
FIG. 20 illustrates a perspective view of a tactile ring.

FIGS. 3, 5 and 7, according to one embodiment, illustrate the housing 110 that encloses the needle assembly 102. The housing 110 includes an inner wall notch 112. As illustrated in FIGS. 7 and 20, the inner wall notch 112 engages an outer diameter 192 of a tactile ring 190. The tactile ring 190 further includes a flange 194 that engages the opening 113 in the septum housing 114 when the needle assembly 102 is in the first position. Thus, the tactile ring 190 axially moves with the housing 110 and indicates to the user when the needle assembly 102 is in the first and second positions.

Figure 10:
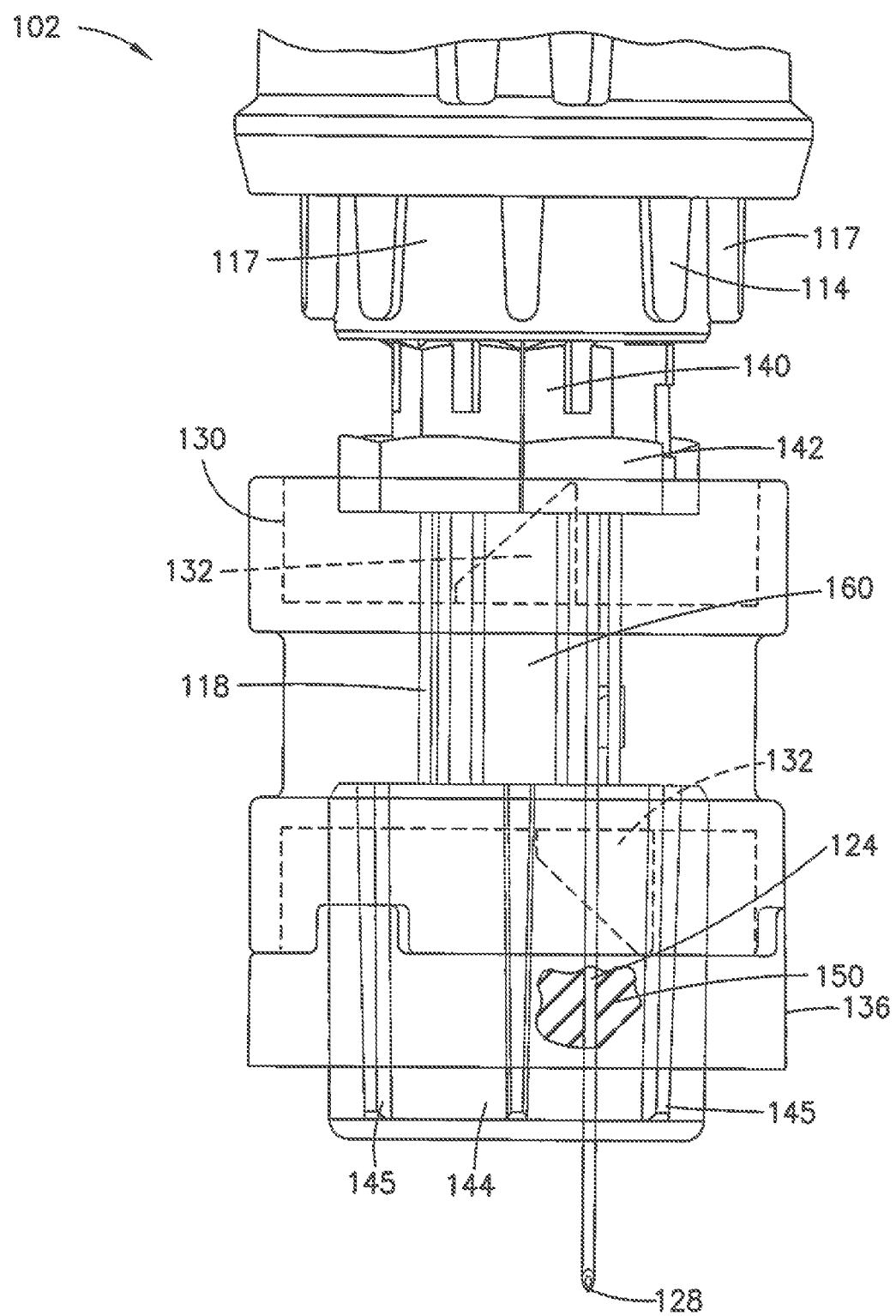
FIG. 10 illustrates a front elevation view of the needle assembly in the second position with various components being transparent for ease of illustration.

According to one embodiment, as illustrated in FIGS. 7 and 10, the user moves the housing 110 to a second position of the needle assembly 102 where the flange 194 of the tactile ring 190 disengages the opening 113 of the septum housing 114, travels downward on the septum housing 114 and engages an indentation where the plurality of external ridges 117 of the septum housing 114 is disposed. Accordingly, a selected needle 124 is withdrawn and exposed from the housing 110 and the selected needle 124 is in fluid communication with the medication delivery pen 104. Thus, the housing 110 moves axially with respect to the septum housing 114.

The needle assembly 102 acts as a magazine for holding the plurality of hollow needles 118. Preferably, seven needles are disposed in the needle assembly 102, although more or fewer is contemplated. When the needle assembly 102 is mounted to the medication delivery pen 104, each of the plurality of needles 118 is disposed in a communication septum 172, 176 and a sealing septum 150 of the needle assembly 102. Specifically, a sharpened proximal end 120 of each of the plurality of needles 118 is disposed in the communication septum 172, 176 and a sharpened distal end 122 of each of the plurality of needles 118 is disposed in the sealing septum 150.

Figure 21:
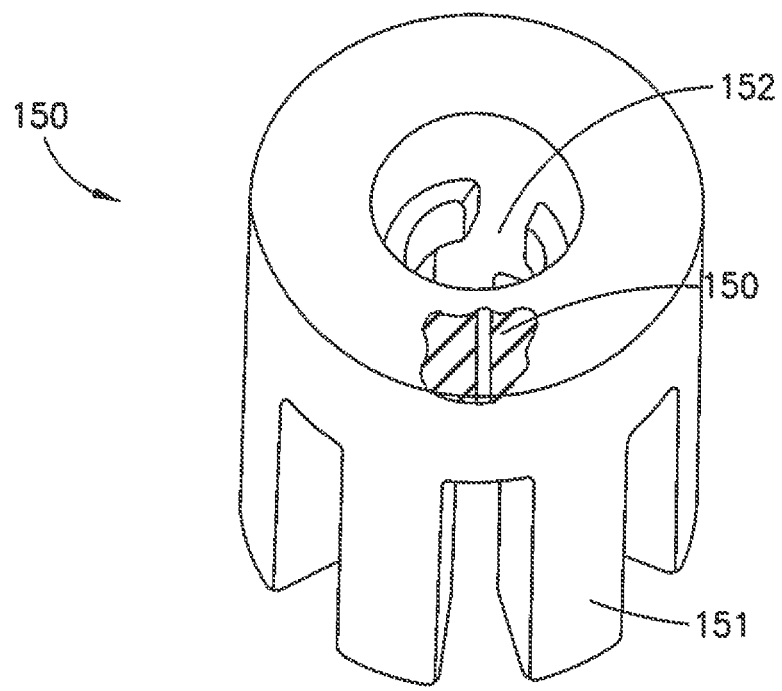
FIG. 21 illustrates a perspective view of a sealing septum.

According to one embodiment, the sealing septum 150, as illustrated in FIG. 21, includes a plurality of seal septum legs 151 and a sealing septum notch 152 that are both used for mounting to a bottom guide 144. The sealing septum 150 of the needle assembly 102 aids to regulate the dispensing of medicament by sealing the plurality of needles 118 at various times during operation. The sealing septum 150 maintains a sterile environment for the plurality of needles 118 before, during and after use. After a needle is used and the needle assembly 102 is in the first position as illustrated in FIG. 5, the sealing septum 150 encloses the distal end 122 and protects the distal end 122 from reuse and injury to the user.

Figure 14:
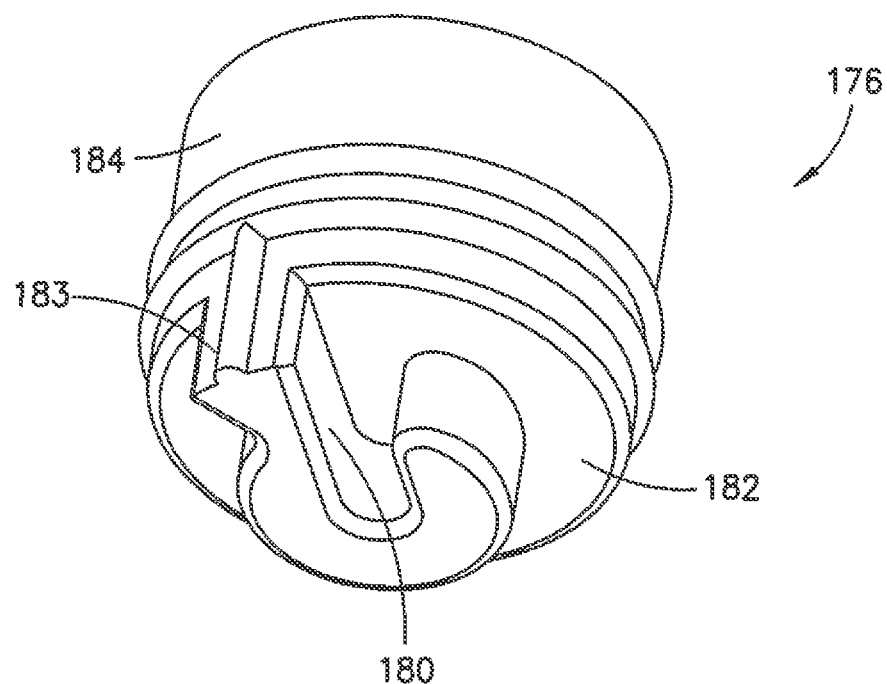
FIG. 14 illustrates a perspective view of an inner septum.

The communication septum 172, 176 according to one embodiment, includes an outer septum 172 and an inner septum 176. The inner septum 176 is disposed at a distal end of the hub 106 and engages the hub mount 105. As illustrated in FIGS. 5, 7 and 14, the inner septum 176 includes a protrusion key 183 and an outer diameter 184 that are secured to the outer septum 172 and provide alignment.

FIG. 14 illustrates the inner septum 176 including a septum chamber comprising a continuous circular cavity 182 and a longitudinal cavity 180. The continuous circular cavity 182 or a curved recess is disposed on a bottom face of the inner septum 176. The circular cavity 182 extends through a circumferential edge of the inner septum 176. The circular cavity 182 extends approximately 315°±30° around the bottom face of the inner septum 176. At one end point of the circular cavity 182, the longitudinal cavity 180 or longitudinal recess extends toward a center of the inner septum 176.

A sharpened distal end of the communication needle 108 pierces the center of the inner septum 176 to establish fluid communication. Specifically, the communication needle 108 allows liquid medicament to flow from the medication delivery pen 104 into the needle assembly 102. The longitudinal cavity 180 of the inner septum 176 establishes fluid communication with the communication needle 108 to fill the septum chamber 180, 182 with medicament.

Figure 15:
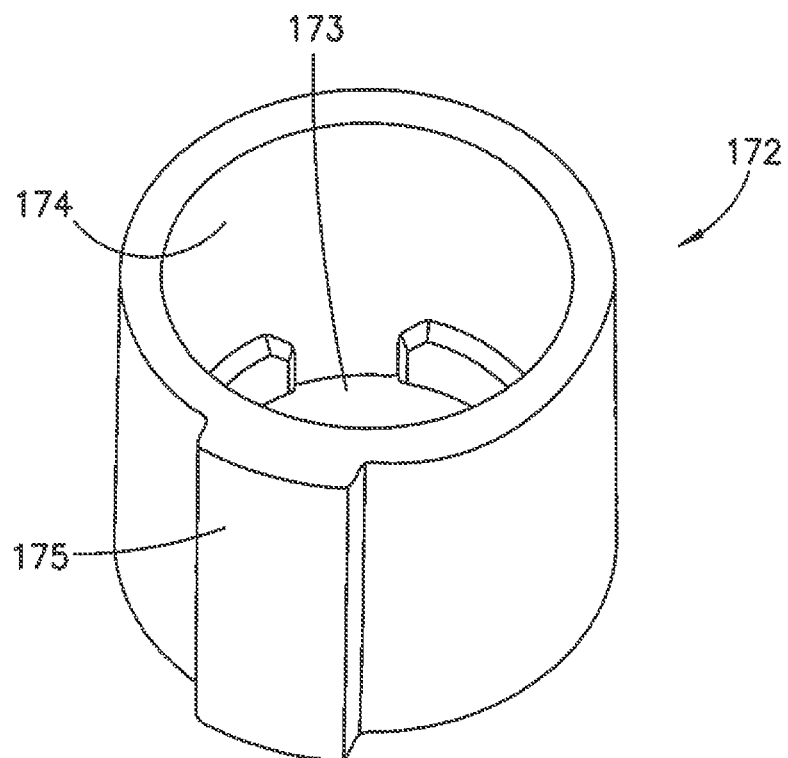
FIG. 15 illustrates a perspective view of an outer septum.

FIG. 15 illustrates the outer septum 172 including an inner diameter notch 173, an inner diameter 174 and an outer diameter protrusion 175. In assembly, the inner diameter 174 of the outer septum 172 engages the outer diameter of the inner septum 176 and provides direct sealing contact. As illustrated in FIG. 5, a passageway is defined between the inner diameter 174 of the outer septum 172 and the circular cavity 182 extending through the circumferential edge of the inner septum 176. This passageway is a sealed area for medicament flow.

The inner septum 176 is secured to the outer septum 172 via an annular snap fit or an interference fit, for example. The outer septum 172 and the inner septum 176 are preferably composed of different materials having different durometers. Such characteristics enhance sealing between the outer diameter 184 of the inner septum 176 and the inner diameter 174 of the outer septum 172.

The inner diameter notch 173 of the outer septum 172 engages the protrusion key 183 of the inner septum 176 during assembly for alignment. Moreover, as illustrated in FIG. 13, the outer diameter protrusion 175 of the outer septum 172 engages the alignment notch 115 of the septum housing 114. Accordingly, the septum housing 114 is aligned to the septum chamber 180, 182.

According to one embodiment, each of the plurality of needles 118 is disposed in the communication septum 172, 174 in the first position of the needle assembly 102. Specifically, in the first position of the needle assembly 102, the proximal end 120 of each of the plurality of needles 118 is disposed in the inner septum 176 which provides needle sterility. As illustrated in FIG. 5, the plurality of needles 118 extends through the circular cavity 182 of the inner septum 176, thus contacting the medicament. However, the plurality of needles 118 is not in fluid communication with the circular cavity 182.

In the second position of the needle assembly 102, at least one of the plurality of needles 118 is exposed for medicament delivery. Specifically, a proximal end 126 of the selected needle 124 is disposed in the circular cavity 182 of the inner septum 176 to be in fluid communication with the medicament received from the communication needle 108. The second position of the needle assembly 102 is described in more detail below.

When the first needle of the plurality of needles 118 is used, the circular cavity 182 is filled with medicament, resulting in the communication septum 172, 176 being primed. Specifically, medicament must traverse and fill the complete fluid path of the circular cavity 182 to reach the first needle of the plurality of needles 118. Accordingly, the incidence of air in the circular cavity 182 is advantageously reduced. Removing air from the fluid path also advantageously improves dose accuracy.

Figure 4:
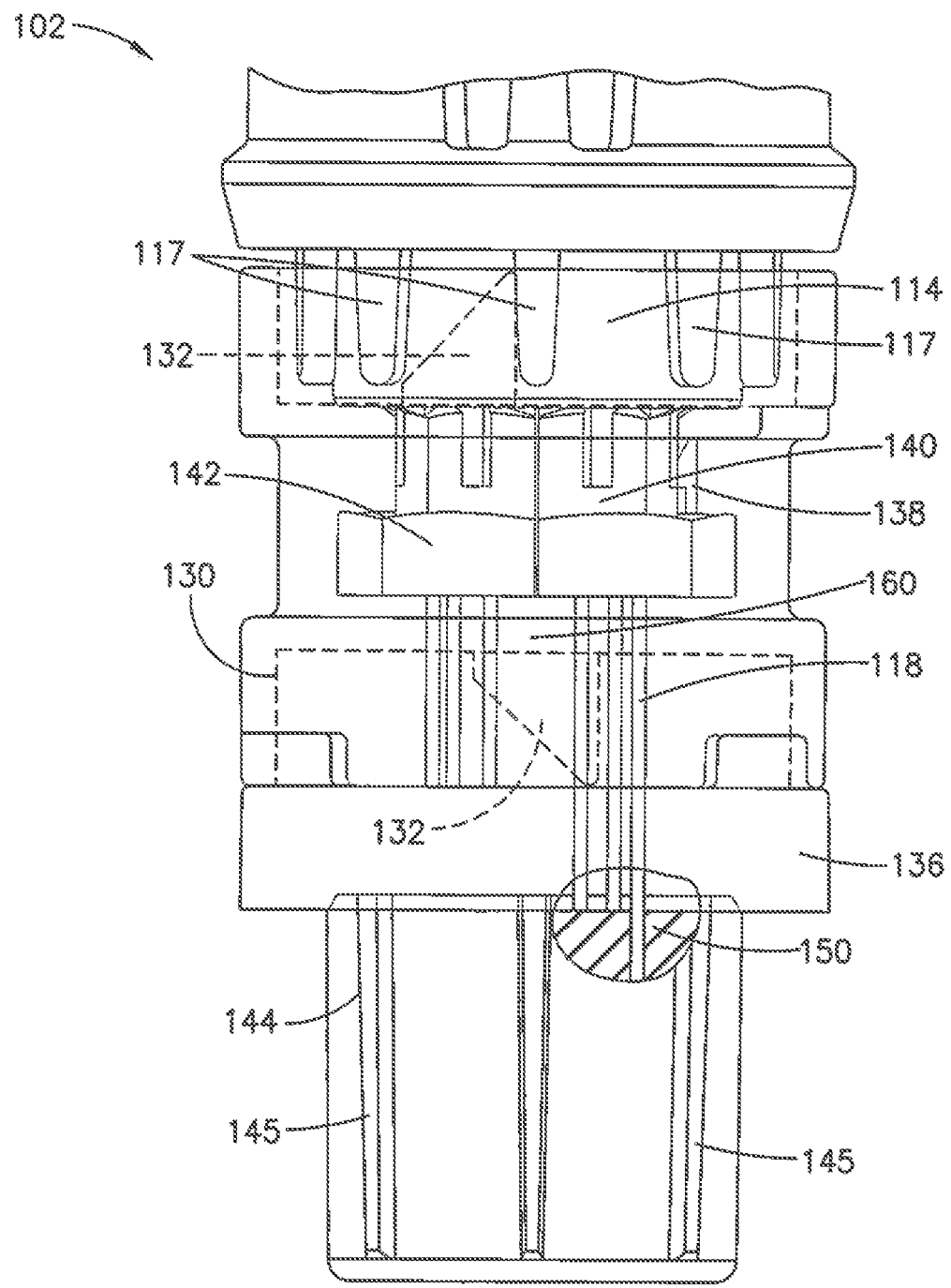
FIG. 4 illustrates a front elevation view of the needle assembly in the first position with various components being transparent for ease of illustration.
Figure 17:
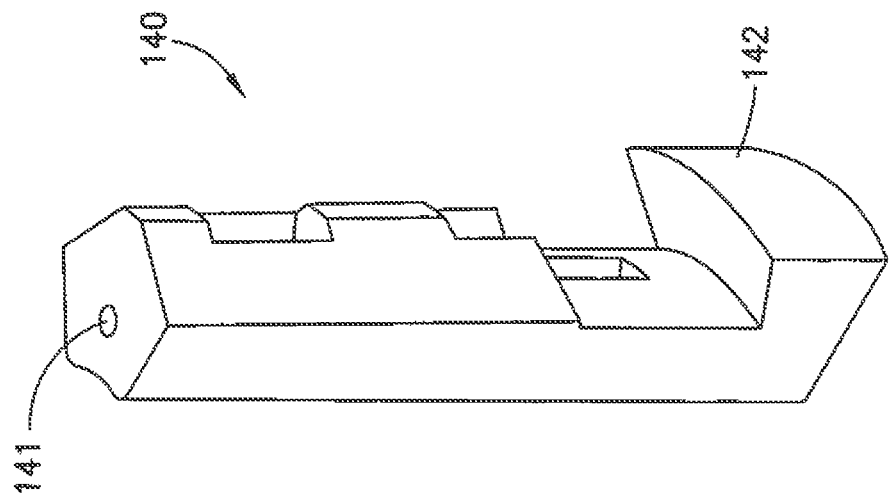
FIG. 17 illustrates a perspective view of a needle post.

According to one embodiment, each of the plurality of needles 118 is secured to a respective needle post 140, as illustrated in FIGS. 4 and 17. Each of the plurality of needles 118 is preferably disposed within a needle post hole 141 of the needle post 140. Each of the plurality of needles 118 is secured to the needle post hole 141 by an adhesive, such as a medical grade adhesive, but other adhesives and other fastening means such a press fit is contemplated. The adhesive is compatible with the material of the plurality of needles 118 and the material of the plurality of needle posts 140. The plurality of needle posts 140 each include an extending portion 142 that aids in operation of the needle assembly 102 as described below.

Figure 16:
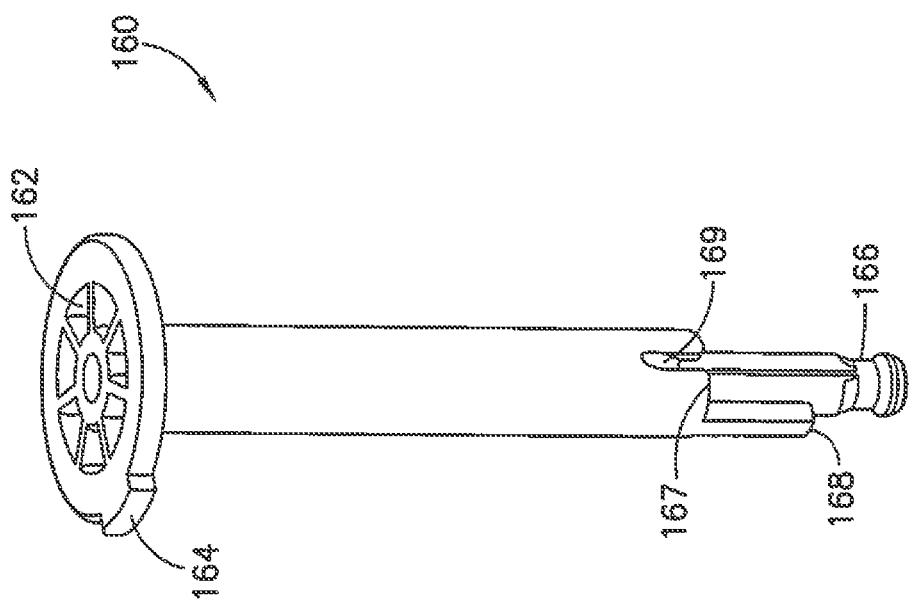
FIG. 16 illustrates a perspective view of a guiding post.

According to one embodiment, the plurality of needles 118 is aligned to the septum housing 114 and the sealing septum 150 by a guiding post 160. FIG. 16 illustrates that the guiding post 160 including a plurality of guide post openings 162 through which each of the plurality of needles 118 axially moves. The plurality of guide post openings 162 is disposed on a circular top face of the guiding post 160. The circular top face also includes a protrusion key 164 that provides alignment to septum housing 114 upon assembly. The plurality of needle posts 140 are arranged around a longitudinal body of the guiding post 160. Specifically, the plurality of needle posts 140 is arranged such that the extending portions 142 extend outward from a centerline of the guiding post 160. Also, the extending portions 142 are each radially aligned with respect to the centerline of the guiding post 160.

The guiding post 160 further includes a guiding post boss 166 that is secured to a bottom guide 144 via an annular snap fit or an interference fit, for example. The guiding post 160 also includes a top ledge 167, a bottom ledge 168 and a guiding post notch 169. As illustrated in FIG. 5, each of these features is used for alignment purposes. Specifically, the top ledge 167 engages the sealing septum notch 152. The guiding post notch 169 engages the bottom guide 144. The bottom ledge 168 bottoms on an alignment notch 147 of the bottom guide 144. Thus, when the guiding post boss 166 is secured to the bottom guide 144, the sealing septum 150 is fixed between the guiding post 160 and the bottom guide 144.

FIGS. 22 and 23 illustrate, according to one embodiment, the needle assembly 102 further including the bottom guide 144. The bottom guide 144 includes an inner diameter 146 that surrounds and supports the sealing septum 150. The bottom guide 144 also includes a webbed cavity 148 and the alignment notch 147. The webbed cavity 148 separates the bottom guide 144 into different sections for each of the plurality of needles 118 to travel through. The webbed cavity 148 also encloses each of the sealing septum legs 151. The alignment notch 147 is disposed between two adjacent sections of the webbed cavity 148.

During assembly, the bottom ledge 168 of the guiding post 160 contacts a top surface of the alignment notch 147. The top ledge 167 of the guiding post 160 contacts the sealing septum notch 152. A portion of the sealing septum notch 152 at a location below the top ledge 167 then contacts a top surface of the webbed cavity 148 of the bottom guide 144. As described above, the sealing septum 150 is thus secured between the guiding post 160 and the bottom guide 144 because the guiding post boss 166 is fixed to the bottom guide 144.

Figure 6:
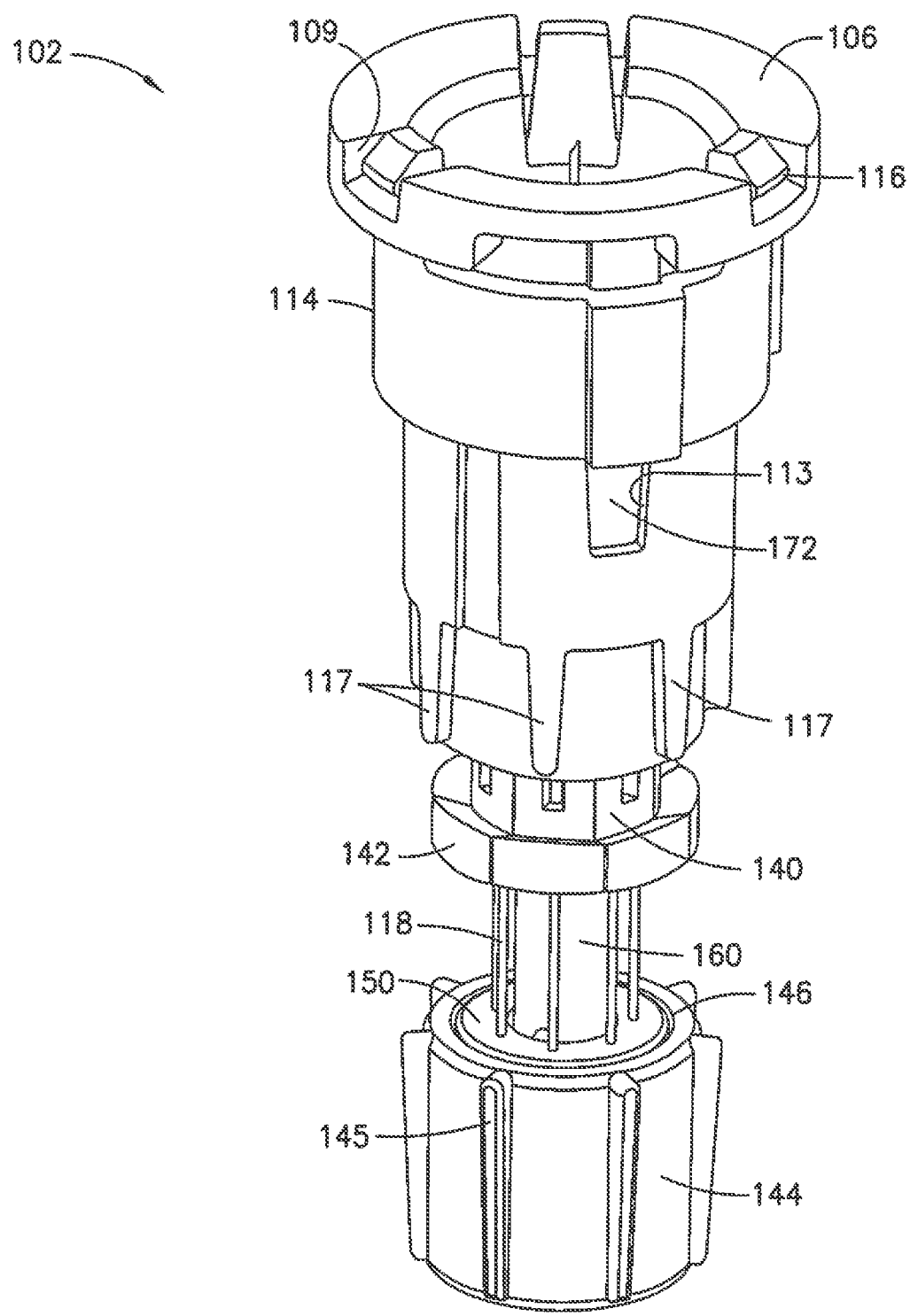
FIG. 6 illustrates a front elevation view of a subassembly of the needle assembly in the first position.

The bottom guide 144 also includes a plurality of external fins 145 being a plurality of external ridges or notches disposed along an outer surface of the bottom guide 144. FIG. 4 illustrates external ridges 145 on the bottom guide 144 and FIG. 6 illustrates a plurality of external notches 145 on the bottom guide 144. The plurality of external tins 145 provides a means to rotate a plurality of needles 118 for use in the needle assembly 102.

Figure 18:
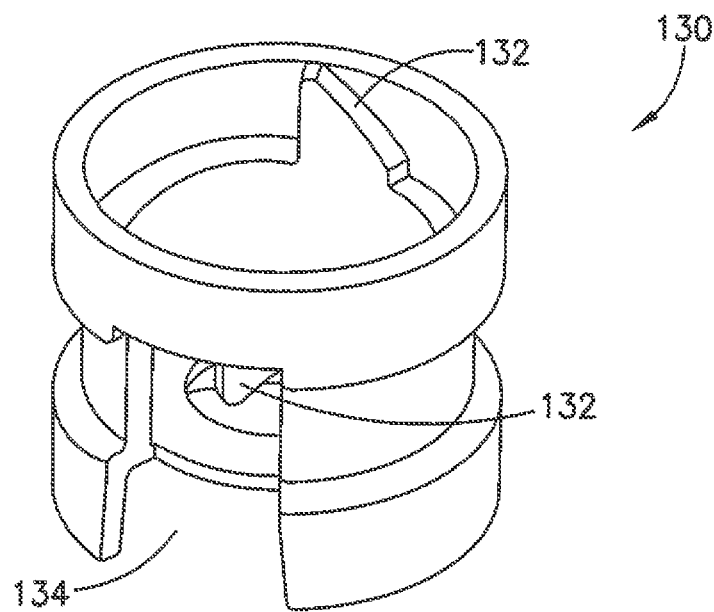
FIG. 18 illustrates a perspective view of a follower ring.

The needle assembly 102 further includes a follower ring 130 that rotates during operation to identify which needle of the plurality of needles 118 is to be selected. According to one embodiment, as illustrated in FIG. 18, the follower ring 130 includes two tooth shaped followers 132 and a side opening 134. The followers 132 are disposed on an inner diameter of the follower ring 130. The followers 132 are circumferentially adjacent to each other although one or the followers 132 is disposed at a top portion of the follower ring 130 and the other follower 132 is disposed at a bottom portion of the follower ring 130. The tooth edge and the tooth tip of each of the followers 132 is oriented in opposite directions and directed away from a center of the follower ring 130.

During operation of the needle assembly 102, the follower 132 on the top portion of the follower ring 130 cooperates with the plurality of external ridges 117 on the septum housing 114. On the other hand, the follower 132 on the bottom portion of the follower ring 130 cooperates with the plurality of external fins 145 on the bottom guide 144. The followers 132 advantageously do not simultaneously engage the plurality of external ridges 117 on the septum housing 114 and the plurality of external fins 145 on the bottom guide 144. Rather, each of the followers 132 is alternately engaged when moving upward and downward between the first and second positions of the needle assembly 102.

Figure 8:
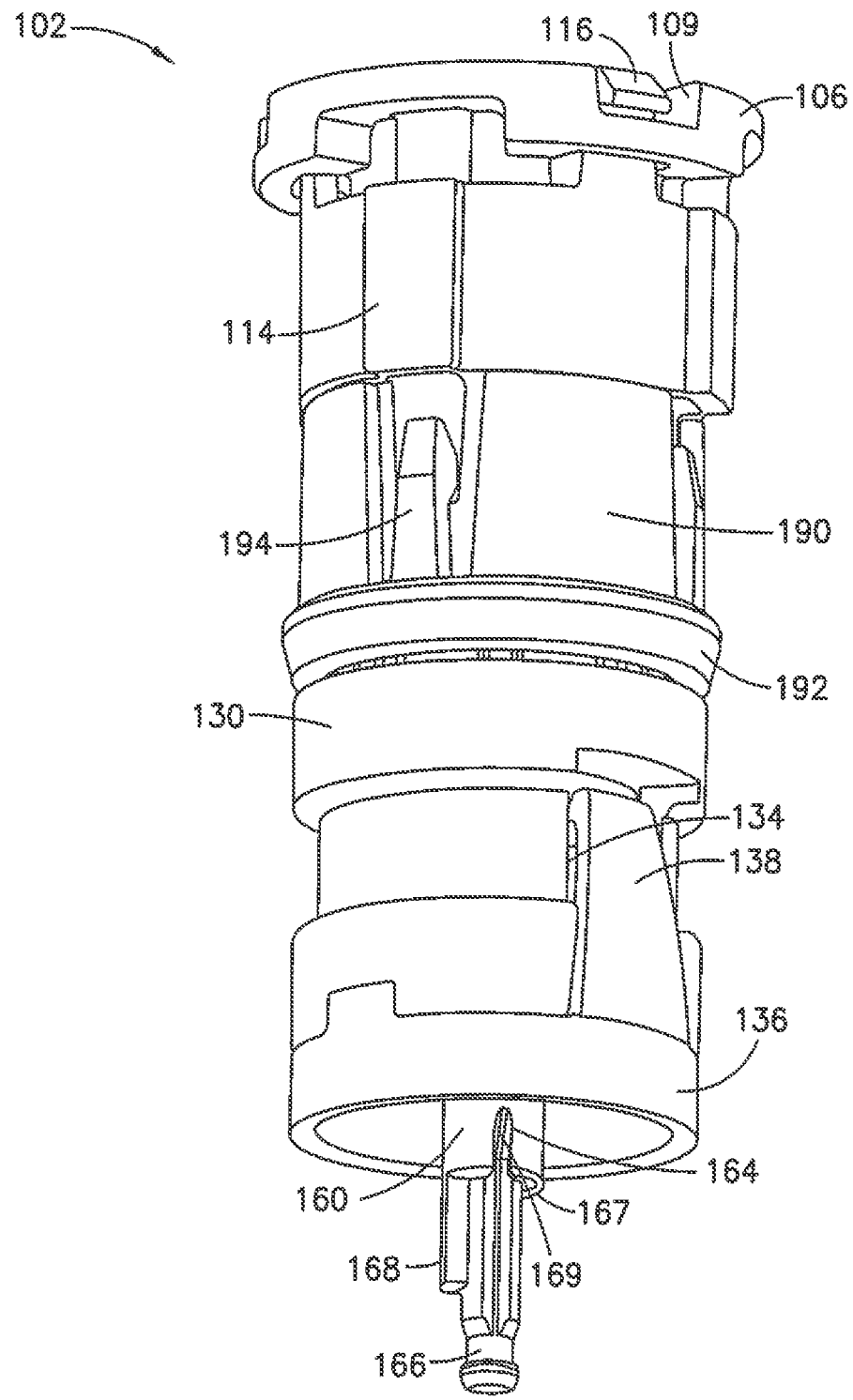
FIG. 8 illustrates a front elevation view of a subassembly of the needle assembly in the first position.

The side openings 134, as illustrated in FIGS. 8 and 18, provides a cavity for engagement with a snap ring 136. Further operation of the followers 132 and the side opening 134 are described below.

Figure 19:
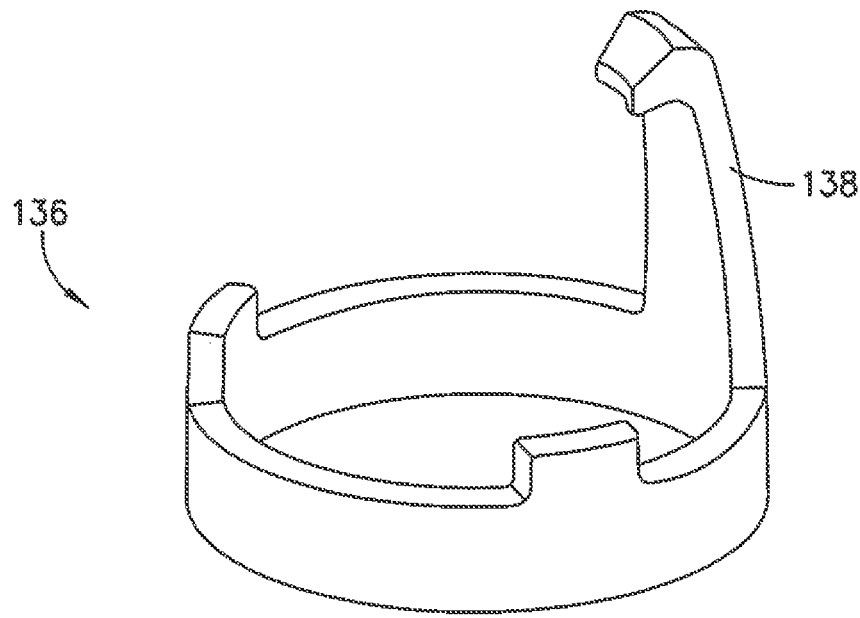
FIG. 19 illustrates a perspective view of a snap ring.

The snap ring 136, according to one embodiment illustrated in FIGS. 8 and 19, is disposed under the follower ring 130. The snap ring 136 includes a snap ring flange 138 and a chamfer. The snap ring flange 138 is disposed in the side opening 134 of the follower ring 130 for engagement and for access to the plurality of needle posts 140. Thus, the follower ring 130 and the snap ring 136 rotate together. The chamfer allows the snap ring flange 138 of the snap ring 136 to elastically deflect in a radial direction and snap over the needle post 140 of the selected needle 124 when the needle assembly 102 travels from the second position to the first position. In operation, when the needle assembly 102 moves from the first position to the second position, the snap ring flange 138 contacts the extending portion 142 of the needle post 140 and applies a force to expose the selected needle 124. The snap ring 136 rotates with respect to the housing 110 but moves axially with the housing 110.

The needle assembly 102, according to one embodiment, further includes a cap 154 secured to the housing 110. The cap 154 and the housing 110 support all of the components of the needle assembly 102. In assembly, the cap 154 engages the housing 110 via a snap-fit joint, for example, and contacts a bottom wall of the housing 110. The cap 154 also includes a hole 155 at its distal end allowing the bottom guide 144 to travel through.

The hole 155 is sized to prevent the bottom guide 144 from exiting the cap 154 and to minimize unauthorized tampering when the needle assembly 102 moves between the first and second positions.

Figure 9:
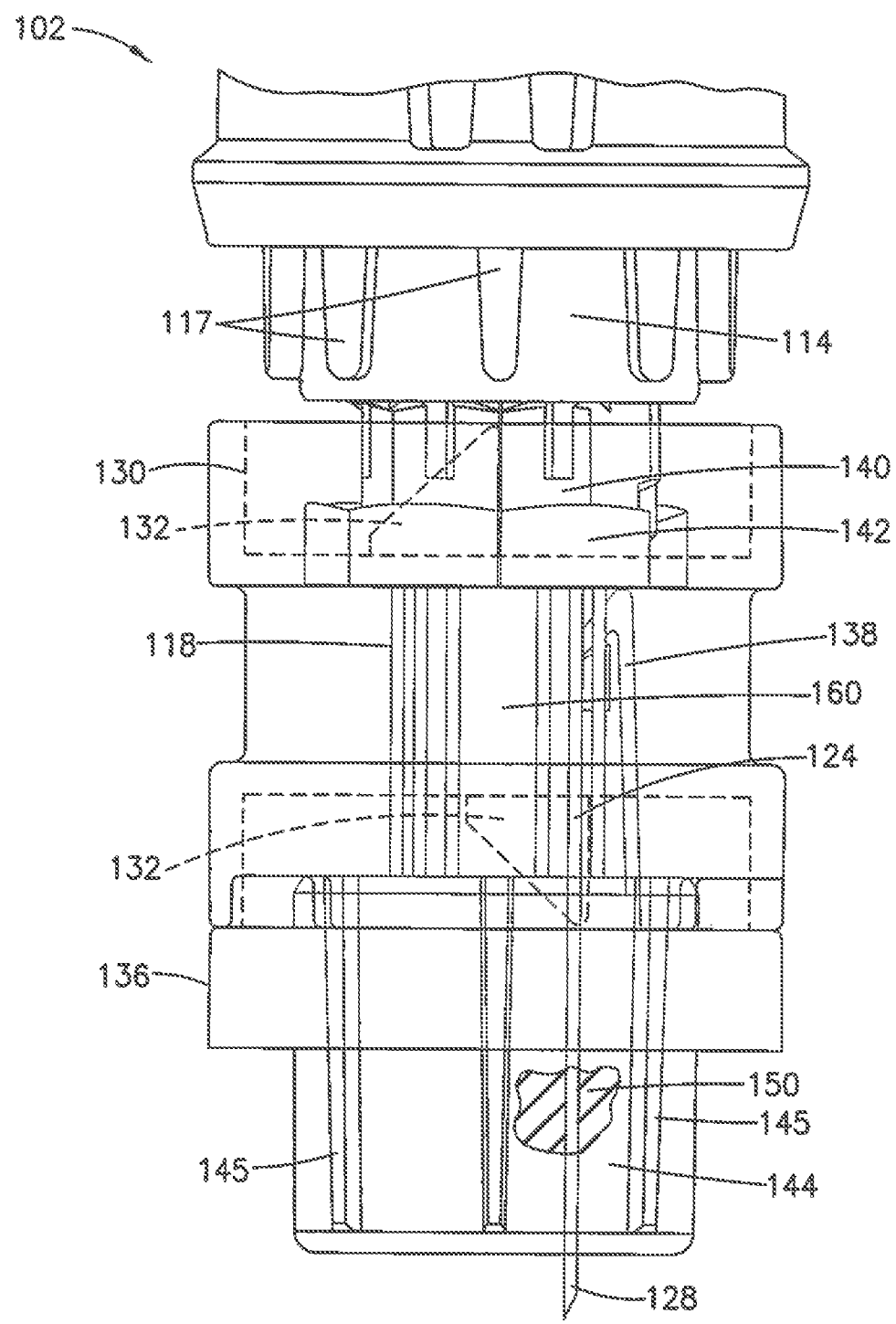
FIG. 9 illustrates a front elevation view of the needle assembly moving from the first position to a second position with various components being transparent for ease of illustration.

The following describes the operation of the needle assembly 102. According to one embodiment, FIG. 9 illustrate the needle assembly 112 moving from the first position and toward the second position where a distal end 128 of the selected needle 124 of the plurality of needles 118 is beginning to be exposed for medicament delivery. As the needle assembly 102 leaves the first position, the distal end 128 of the selected needle 124 begins to pierce the sealing septum 150 and the remaining plurality of needles 118 are all sealed and sterilized in the sealing septum 150 of the needle assembly 102.

As illustrated in FIGS. 7 and 8, when the housing 110 moves downward, the follower ring 130 and the snap ring 136 move downward as well. As the follower ring 130 moves downward as illustrated in FIG. 9, the follower 132 at the bottom portion of the follower ring 130 engages one of the plurality of external fins 145 of the bottom guide 144. Specifically, the follower 132 contacts one of the plurality of external fins 145 and the follower 132 slides along its tooth shaped edge to rotate the follower ring 130 while maintaining contact with the external fin 145.

As described above, the snap ring 136 also rotates because the snap ring 136 is rotationally connected to the follower ring 130. Since the snap ring 136 is rotationally coupled to the follower ring 130, the flange 138 of the snap ring 136 applies pressure the extending portion 142 of the needle post 140 of the selected needle 124. This causes the distal end 128 of the selected needle 124 to pierce the sealing septum 150 of the needle assembly 102 and expose the selected needle 124 for medication delivery.

FIG. 10 illustrate the needle assembly 102 in the second position where the selected needle 124 amongst the plurality of needles 118 is exposed for medicament delivery. Specifically, the follower 132 has completed rotation and is between external fins 145 of the bottom guide 144. The distal end 128 of the selected needle 124 is ready for medication delivery. In this position, as described above, the proximal end 126 of the selected needle 124 enters into fluid communication with the septum chamber 180, 182 and a sharpened distal end 128 of the selected needle 124 pierces the sealing septum 150 and is exposed.

Figure 10A:
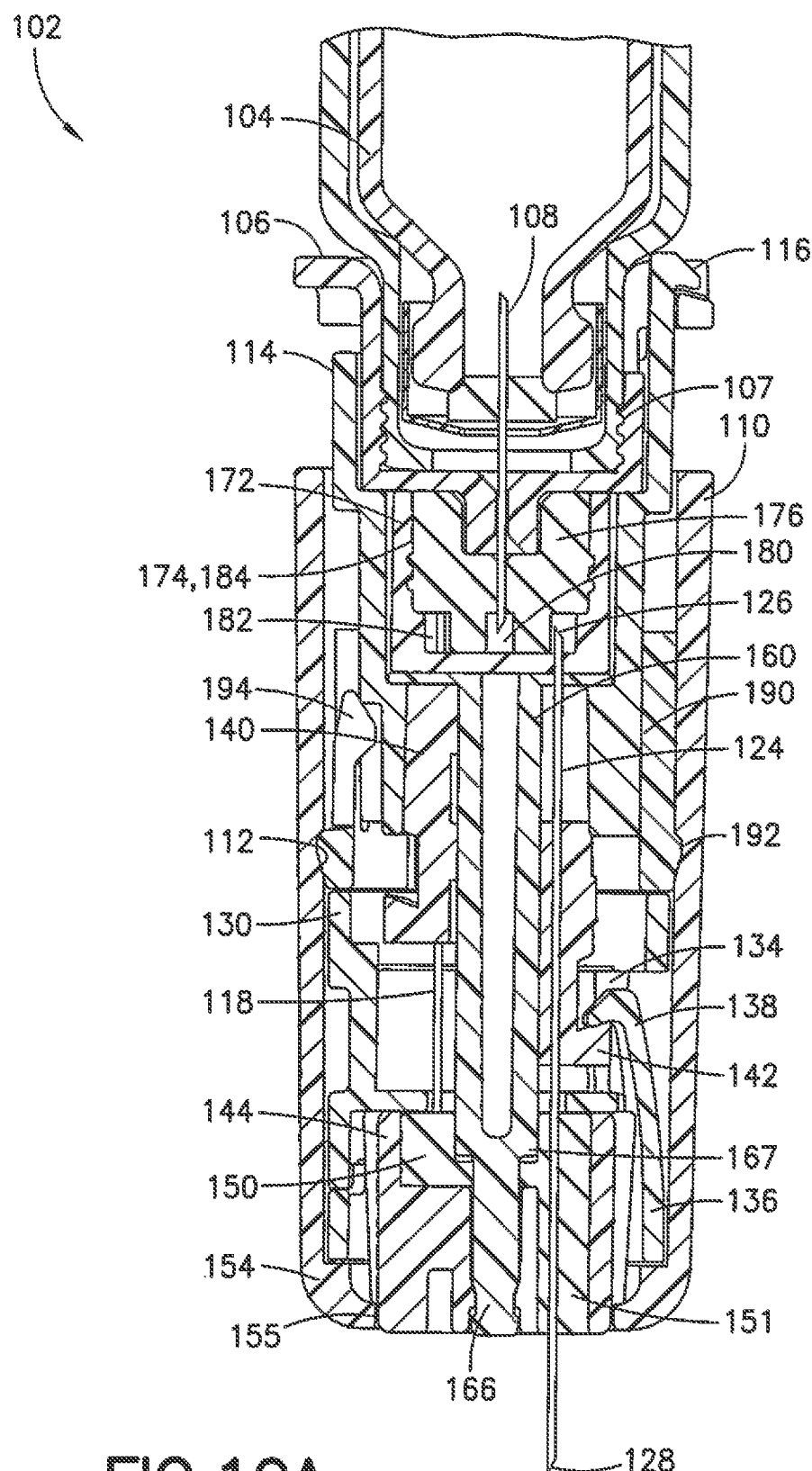
FIG. 10A illustrates a cross sectional view of the needle assembly in the second position.

FIG. 10A illustrates the proximal end 126 of the selected needle 124 in fluid communication with the circular cavity 182 of the septum chamber 180, 182. Each of the plurality of needles 118 is aligned and configured to be in fluid communication with the septum chamber 180, 182 when selected by the snap ring 136.

The proximal end 120 of the remaining needles 118 continues to be disposed in the inner septum 176. The distal end 122 of the remaining needles 118 also continues to stay sealed and sterilized in the sealing septum 150 of the needle assembly 102.

During operation, although the selected needle 124 moves axially, the selected needle 124 does not move radially. In fact, none of the plurality of needles 118 substantially moves radially or rotates at any point during operation. No substantial radial or rotational movement in this regard is understood as 0±5% with respect to a centerline of the needle assembly 102. Preferably, one skilled in the art understands that substantial in this context means that no radial or rotational movement is required to perform the intended function. However, slight radial or rotational movement may be desired to ensure the proper spacing of parts for smooth operation and proper movement of the plurality of needles 118 axially without jamming. This configuration improves simplicity of the design and reduces movement of parts in the needle assembly 102.

The user cannot draw the housing 110 out from the needle assembly 102 any further than the second position of the needle assembly 102 because of the configuration illustrated in FIG. 5. Specifically, a bottom surface of the follower ring 130 contacts a top surface of the cap 154 and prevents further axial movement of the needle assembly 102. The cap 154 and the bottom guide 144 also contact a patient delivery site during needle insertion and injection to restrict further axial movement.

Figure 11:
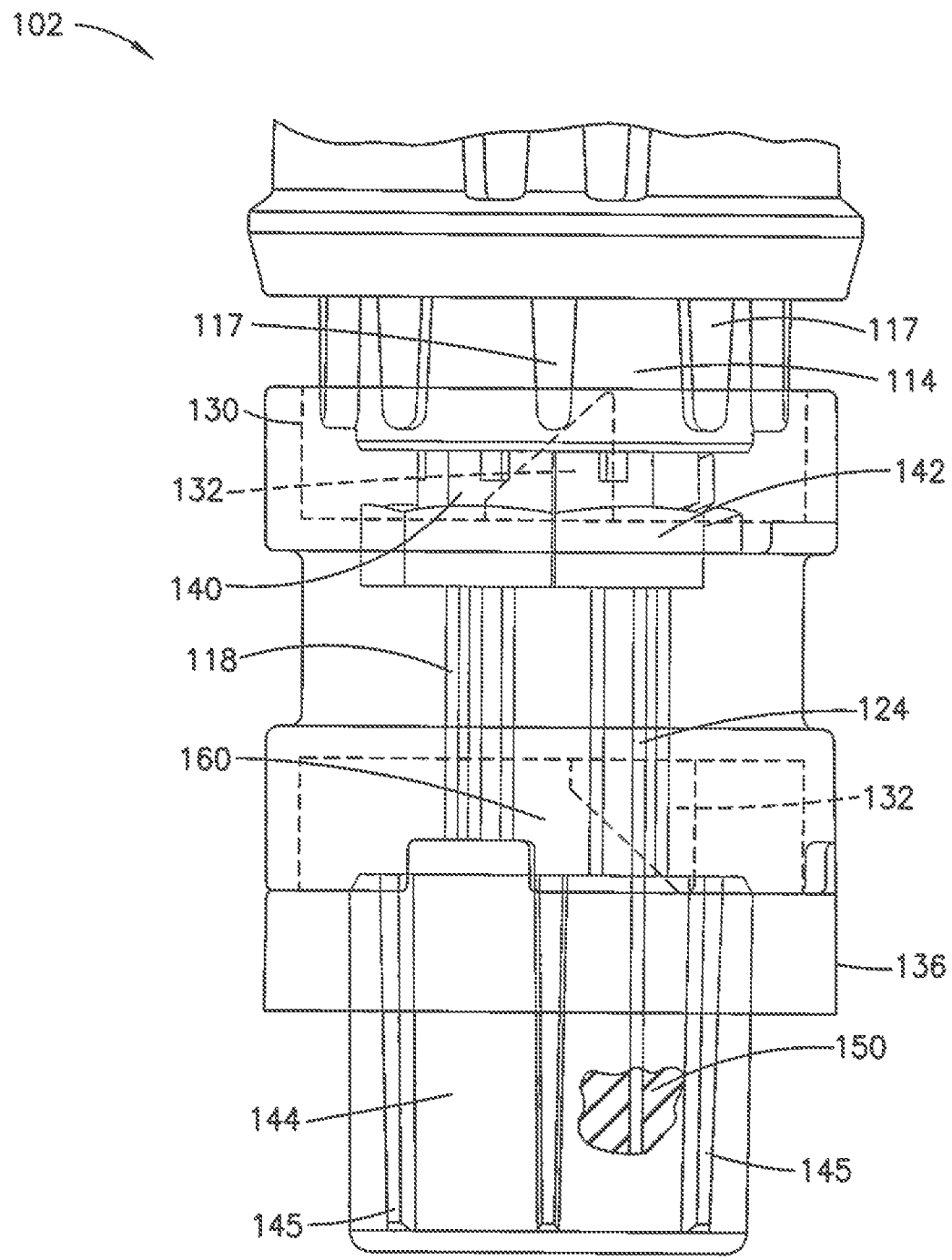
FIG. 11 illustrates a front elevation view of the needle assembly moving from the second position to the first position with various components being transparent for ease of illustration.

FIG. 11 illustrates the needle assembly 102 returning from the second position back to the first position when the user pulls the housing 110 back toward the medication delivery pen 104. At the same time, the cap 154 pushes the snap ring 136 and the follower ring 130 upwards which moves the extending portion 142 of the selected needle 124 upward. The distal end 128 of the selected needle 124 returns into the sealing septum 150 of the needle assembly 102. The sealing septum 150 encloses the selected needle 124 and protects the user.

Meanwhile, the follower 132 at the top portion of the follower ring 130 contacts one of the plurality of external ridges 117 of the septum housing 114 and causes the follower ring 130 to rotate. FIG. 11 illustrates the follower 132 at the top portion of the follower ring 130 contacting one of the plurality of external ridges 117 of the septum housing 114 and the follower 132 slides along its tooth shaped edge to rotate the follower ring 130 while maintaining contact with the external ridge 117.

As the needle assembly 102 returns to the first position, the follower ring 130 rotates and prepares the flange 138 of the snap ring 136 to align with an adjacent needle of the plurality of needles 118 for a subsequent injection. Specifically, the chamfer of the snap ring 136 allows the flange 138 to elastically deflect in a radial direction and snap over the extending portion 142 of the needle post 140 of the adjacent needle of the plurality of needles 118. In this manner, the next needle in the needle assembly 102 is ready for subsequent use.

FIGS. 4 and 5 illustrate the needle assembly 102 after it has returned back to the first position where the distal ends 122 of each of the plurality of needles 118 are retracted and disposed in the sealing septum 150 of the needle assembly 102. The flange 138 of the snap ring 136 is now rotated and aligned to downwardly push the extending portion 142 of the needle post 140 of the subsequent needle amongst the plurality of needles 118 when the housing 110 again moves from the first position to the second position.

The process of moving from the first position to the second position and back to the first position while rotating the snap ring 136 repeats in the manner describe above so that each needle amongst the plurality of needles 118 is individually exposed in a consecutive manner from a first needle, to each adjacent needle and to a last needle. The external ridges 117 of the septum housing 114 and the plurality of external fins 145 on the bottom guide 144 are configured so that each of the plurality of needles 118 are only used once.

FIG. 24, according to one embodiment, illustrates the cover 156 that encloses the needle assembly 102. The cover 156 is sealed with a teardrop label 158 to seal the needle assembly 102 and maintain its sterility for transportation and security purposes prior to operating with the medication delivery pen 104. When the needle assembly 102 is ready for use, the user peels off the teardrop label 158 and removes the needle assembly 102 from the cover 156.

Figure 31:
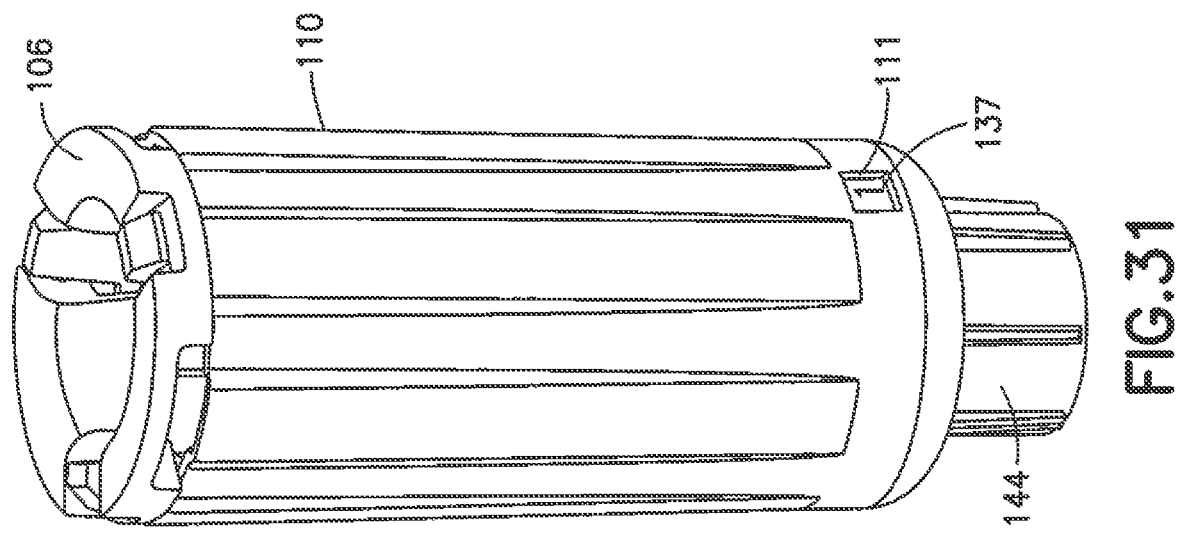
FIG. 31 illustrates the needle assembly of FIG. 25 with the counter indicating 1 needle remains to be used.
Figure 32:
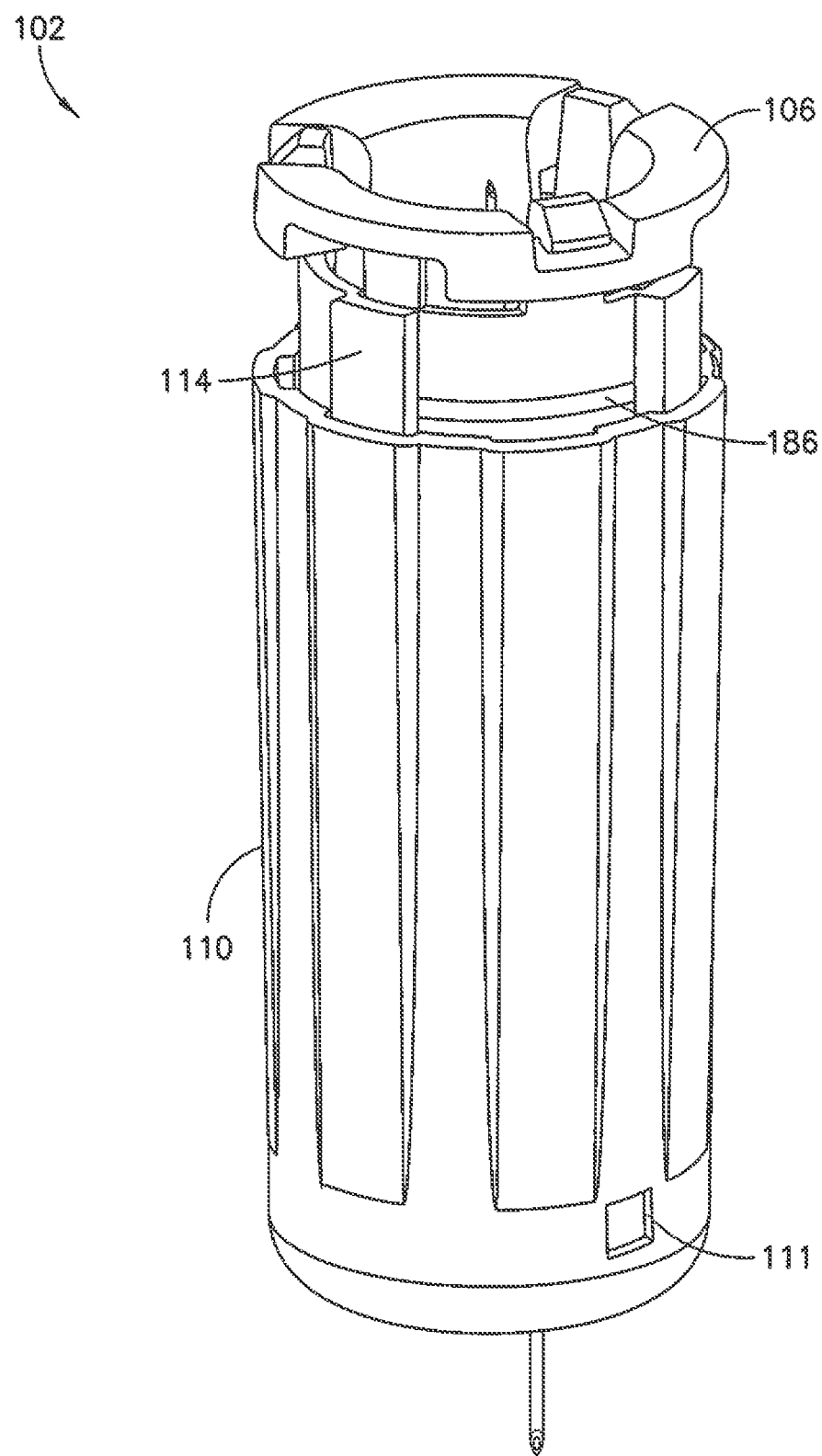
FIG. 32 illustrates the needle assembly of FIG. 25 having the contrast band visible in the second position.

In another embodiment, as illustrated in FIGS. 25-32, the needle assembly 102 functions in a similar manner as described in the embodiments above but also includes a needle counter and a contrast band or indicator 186 that visually displays to the user that the Ball length of the selected needle 124 is exposed. Specifically, as illustrated in FIG. 32, the contrast band 186 is a colored paint, for example, that is applied to an outer surface of the septum housing 114.

Figure 26:
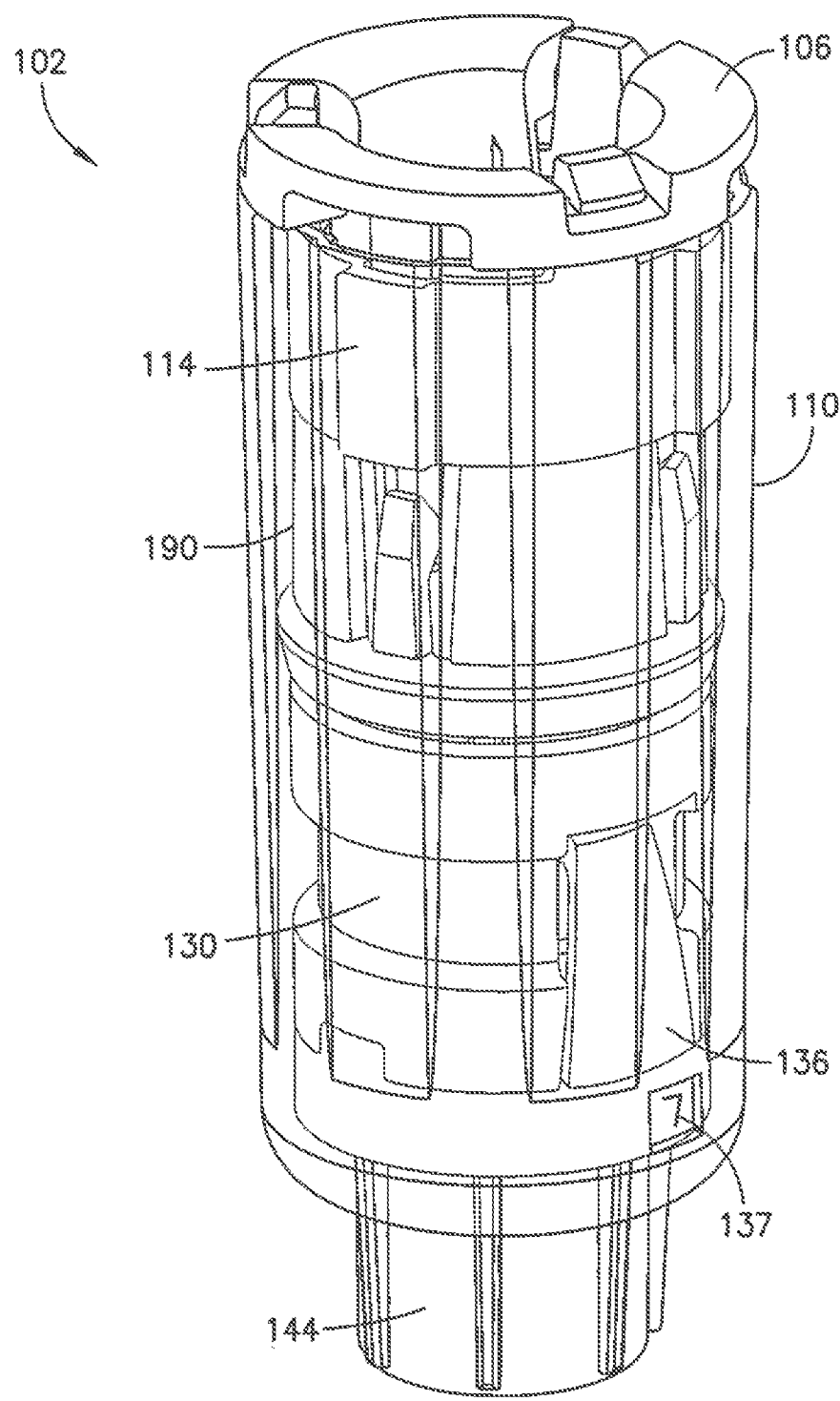
FIG. 26 illustrates the needle assembly of FIG. 25 with a housing being transparent.
Figure 27:
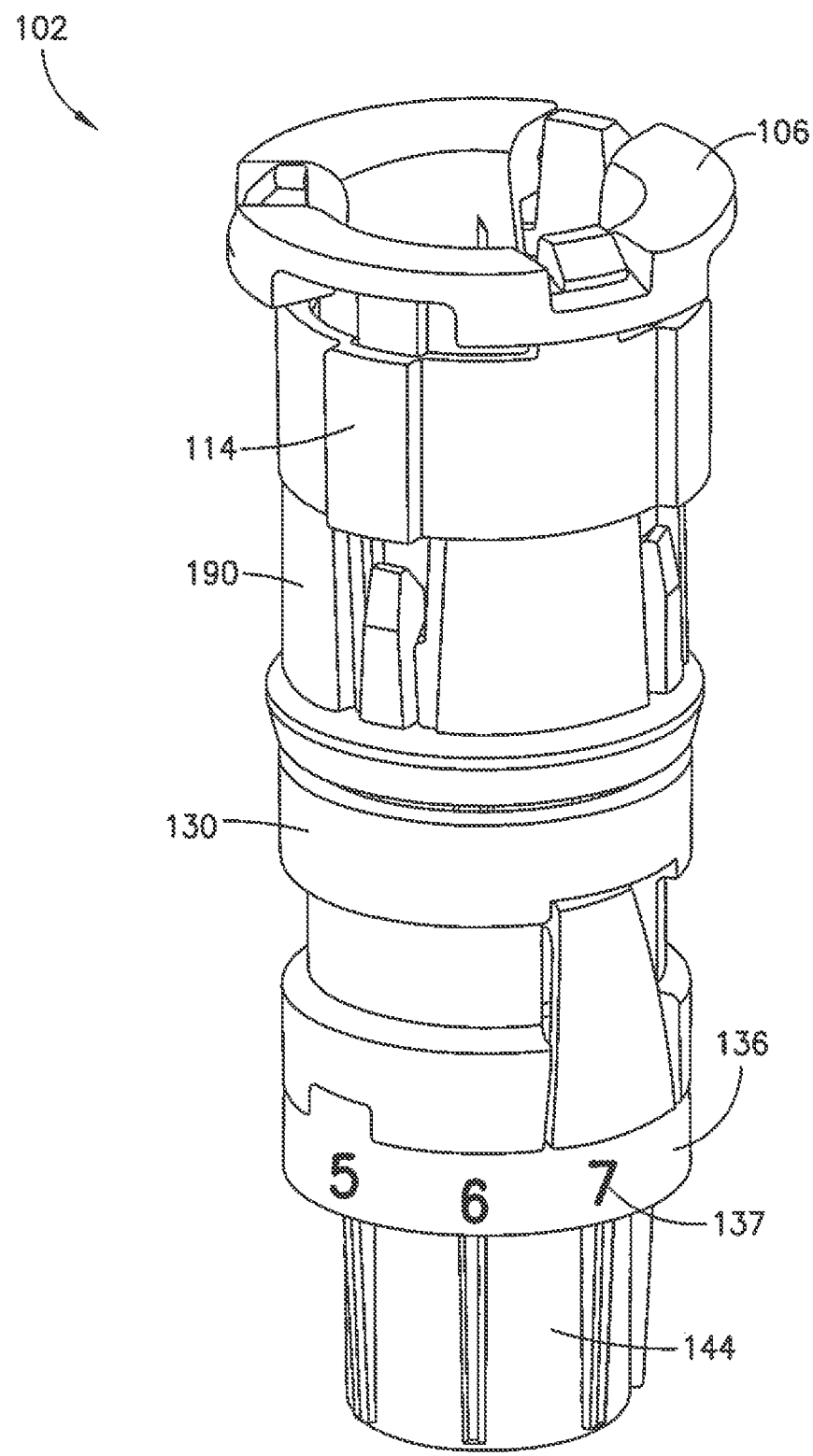
FIG. 27 illustrates the needle assembly of FIG. 25 with the housing removed.
Figure 28:
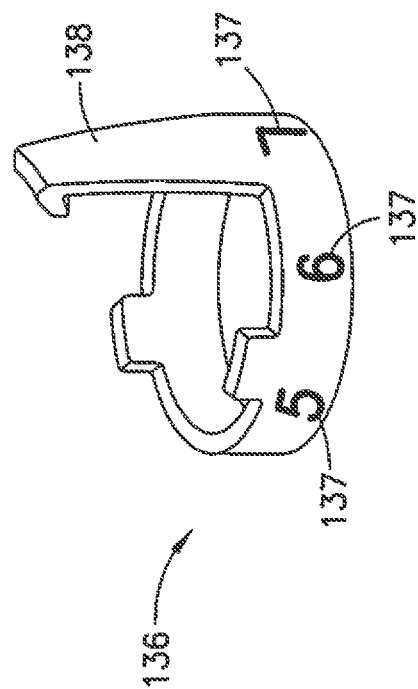
FIG. 28 illustrates a snap ring in the needle assembly of FIG. 25.

The housing 110 of FIGS. 25-32 includes a window 111 and an exterior surface of the snap ring 136 includes a plurality of needle numbers 137. As illustrated in FIG. 28, the exterior surface of the snap ring 136 includes the plurality of needle numbers 137 horizontally arranged and sequentially ordered around the snap ring 136 to indicate how many of the plurality of needles 118 are unused. The window 111 displays one of the plurality of needle numbers 137 at a time. The operation of the features in this embodiment is described below.

Figure 25:
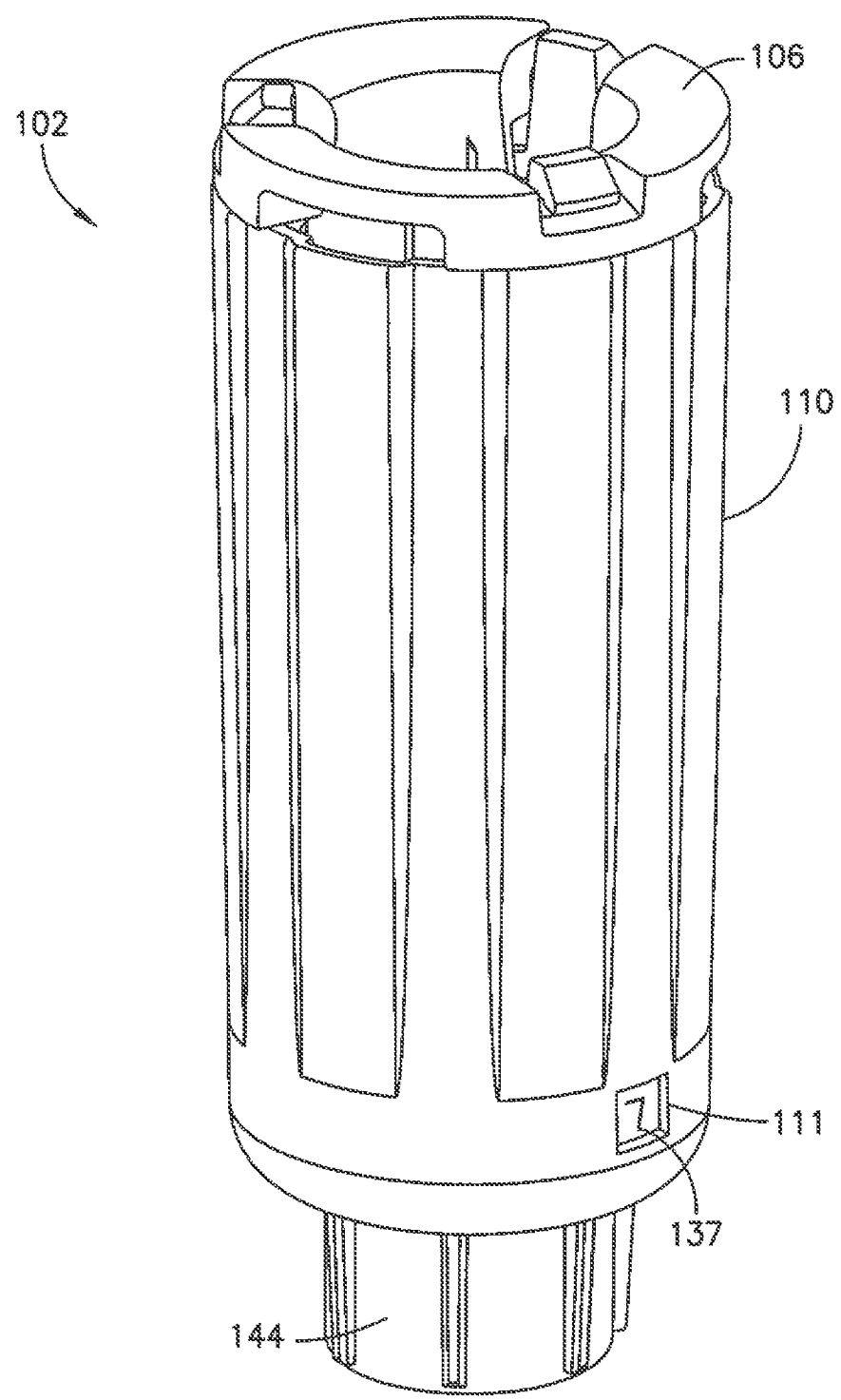
FIG. 25 illustrates an alternate embodiment of a needle assembly having a contrast band in the first position and a counter indicating that 7 needles remain to be used.

FIG. 25 illustrates that the housing 110 covers the contrast band 186 and the septum housing 114 when the needle assembly 102 is not in use (the housing 110 is in the first position). In this position, the window 111 of the housing 110 displays one of the plurality of needle numbers 137 (e.g., "7") on the snap ring 136.

FIG. 26 illustrates the needle assembly 102 with the housing 110 being transparent and FIG. 27 illustrates the needle assembly 102 with the housing 110 removed. These figures illustrate how the snap ring 136 of FIG. 28 operates within the needle assembly 102.

As the user begins to move the housing 110 toward the second position, the window 111 in the housing 110 also moves and begins to display the outer surface of the bottom guide 144. As illustrated in FIG. 32, when the housing 110 reaches the second position, the contrast band 186 is exposed. This indicates to the user that the selected needle 124 in the needle assembly 102 is fully extended and ready for medication delivery. Also, the window 111 in the housing 110 extends beyond the bottom guide 144 to display nothing.

Figure 29:
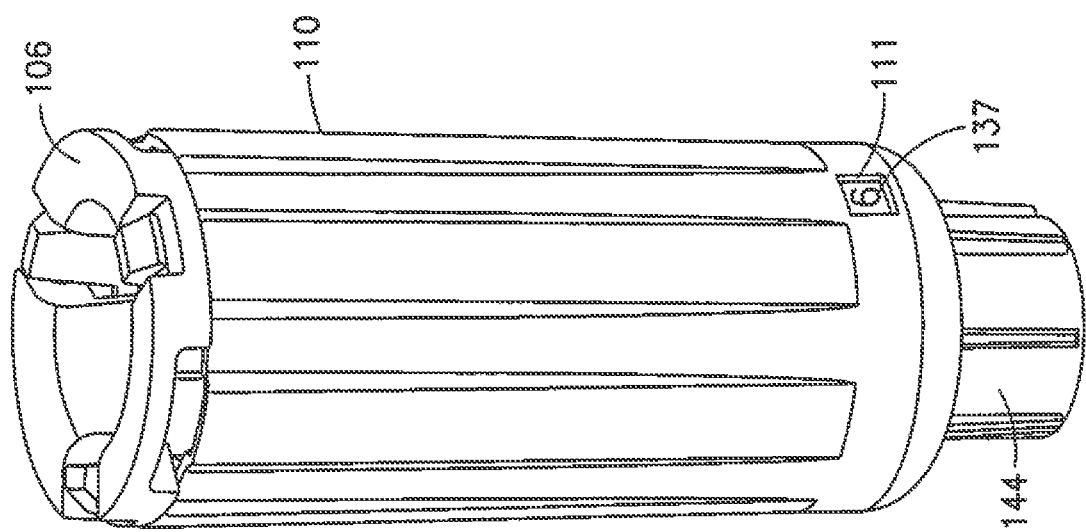
FIG. 29 illustrates the needle assembly of FIG. 25 with the counter indicating 6 needles remain to be used.
Figure 30:
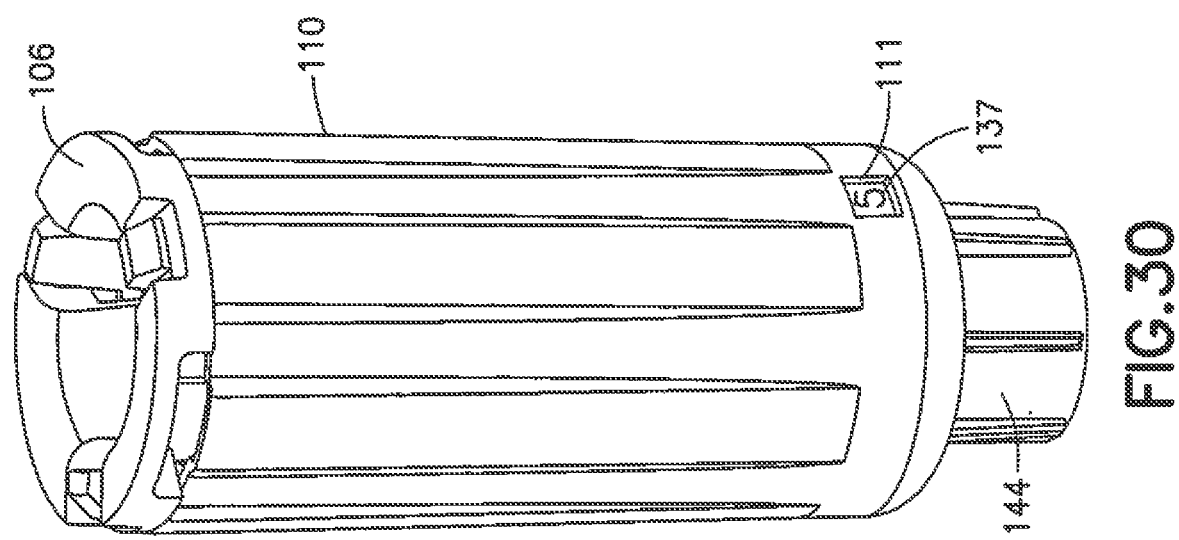
FIG. 30 illustrates the needle assembly of FIG. 25 with the counter indicating 5 needles remain to be used.

When the housing 110 is returned to the first position, the snap ring 136 rotates in the manner described in the embodiments above to prepare the next needle for injection. As a result, FIG. 29 illustrates that a subsequent needle number (e.g., "6") of the plurality of needle numbers 137 is displayed through the window 111 of the housing 110. The plurality of needle numbers 137 are arranged sequentially on the snap ring 136 so that every time one of the plurality of needles 118 is used, the needle number 137 is sequentially reduced and displayed through the window 111 of the housing 110. Specifically, FIGS. 30 and 31 illustrate the needle number being reduced down to 5 after the next use and ultimately down to 1 after six of the seven needles are used.

In another embodiment, the septum housing 114 can include contrast bands 186 that are black and red. The black contrast band is exposed immediately when the housing 110 begins to move to the second position. The red contrast band is not visible in FIG. 32 because it is underneath the housing 110. The red contrast band is exposed when the needle reaches its maximum stroke length of 4 mm or 5 mm, for example. Thus, the black contrast band is disposed above the red contrast band.

Alternately, the needle assembly 102 includes multiple contrast bands 186 that indicate a different needle length exposed. Specifically, various colors of contrast bands 186 can be sequentially exposed as the housing 110 moves from the first to the second position to indicate various needle stroke lengths. For example, contrasts bands 186 in colors of red, orange, yellow, green and blue represent a needle stroke length of 1 mm, 3 mm, 4 mm and 5 mm, respectively. Each of these contrasts bands is consecutively displayed as the housing 110 moves from the first position to the second position.

FIG. 32 illustrates one black contrast band 186. However, it is readily apparent to one skilled in the art in view of the description above on how multiple contrast bands 186 can be applied.

The foregoing detailed description of the certain exemplary embodiments has been provided for the purpose of explaining the principles of the invention and its practical application, thereby enabling others skilled in the art to understand the invention for various embodiments and with various modifications as are suited to the particular use contemplated. This description is not necessarily intended to be exhaustive or to limit the invention to the precise embodiments disclosed. Any of the embodiments and/or elements disclosed herein may be combined with one another to form various additional embodiments not specifically disclosed, as long as they do not contradict each other. Accordingly, additional embodiments are possible and are intended to be encompassed within this specification and the scope of the invention. The specification describes specific examples to accomplish a more general goal that may be accomplished in another way.

As used in this application, the terms "front," "rear," "upper," "lower," "upwardly," "downwardly," and other orientational descriptors are intended to facilitate the description of the exemplary embodiments of the present invention, and are not intended to limit the structure of the exemplary embodiments of the present invention to any particular position or orientation. Terms of degree, such as "substantially" or "approximately" are understood by those of ordinary skill to refer to reasonable ranges outside of the given value, for example, general tolerances associated with manufacturing, assembly, and use of the described embodiments.

The invention claimed is:

1. An attachable needle assembly for use on a medication delivery pen, the needle assembly comprising:
    a housing enclosing:
        a hub being fixed to a communication needle, the hub being configured to engage the medication delivery pen and the communication needle being configured to pierce a reservoir septum of the medication delivery pen;
        a communication septum of the needle assembly defining a septum chamber, the septum chamber of the needle assembly being in continuous fluid communication with the communication needle;
        a plurality of needles disposed in the communication septum of the needle assembly;
        a follower ring that rotates and identifies which needle of the plurality of needles is to be selected; and
        a snap ring that applies a force to expose the selected needle and move the selected needle to be in fluid communication with the septum chamber of the communication septum of the needle assembly, wherein
    when the housing is in a first position, the plurality of needles is not exposed, and when the housing is in a second position, the selected needle of the plurality of needles is in fluid communication with the septum chamber of the communication septum of the needle assembly and exposed for medicament delivery.

2. The attachable needle assembly of claim 1, wherein the communication septum of the needle assembly includes an inner septum and an outer septum, the inner septum is sealed within the outer septum.

3. The attachable needle assembly of claim 2, wherein the inner septum includes the septum chamber, the septum chamber comprising a circular cavity and a longitudinal cavity that carries medicament from the communication needle and fluidly communicates with the selected needle of the plurality of needles in the second position.

4. The attachable needle assembly of claim 2, wherein in the first position, each of a proximal end of the plurality of needles is disposed in the inner septum and each of a distal end of the plurality of needles is disposed in a sealing septum.

5. The attachable needle assembly of claim 2, wherein in the second position, a proximal end of each of a remaining plurality of needles is disposed in the inner septum.

6. The attachable needle assembly of claim 1, wherein in the second position, a proximal end of the selected needle of the plurality of needles is in fluid communication with the septum chamber.

7. The attachable needle assembly of claim 1, wherein
    each of the plurality of needles is secured in a respective needle post; and
    the snap ring includes a flange that contacts and moves one of the plurality of needle posts to expose a distal end of the selected needle when the housing is in the second position.

8. The attachable needle assembly of claim 1, wherein the follower ring includes an opening that mates with a flange of the snap ring.

9. The attachable needle assembly of claim 1, further comprising
    a guiding post that orients a plurality of needle posts; and
    the plurality of needle posts each include an extending portion, wherein
    the guiding post arranges the plurality of needle posts such that the extending portions extend outward from a centerline of the guiding post.

10. The attachable needle assembly of claim 1, wherein the follower ring rotates with respect to the housing and moves axially with the housing when the housing travels between the first position and the second position.

11. The attachable needle assembly of claim 1, further comprising a tactile ring that engages a septum housing and the housing to ensure that the follower ring axially moves with respect to the housing.

12. The attachable needle assembly of claim 1, wherein
the follower ring includes two tooth shaped followers;
the plurality of needles are disposed in a guiding post, the guiding post is fixed to a bottom guide having a plurality of external fins; and
the communication septum is disposed in a septum housing having a plurality of external ridges, wherein
the tooth shaped followers of the follower ring contact the plurality of external fins of the bottom guide and the plurality of external ridges of the septum housing to rotate the follower ring.

13. The attachable needle assembly of claim 12, wherein the tooth shaped followers alternate contact with the plurality of external fins of the bottom guide and the plurality of external ridges of the septum housing to rotate and select each needle consecutively from a first needle to a last needle of the plurality of needles.

14. The attachable needle assembly of claim 12, wherein when the housing is moving from the first position to the second position, one of the two tooth shaped followers contacts one of the plurality of external fins of the bottom guide and causes the follower ring to rotate.

15. The attachable needle assembly of claim 12, wherein when the housing is moving from the second position to the first position, one of the two tooth shaped followers contacts one of the plurality of external ridges of the septum housing and causes the follower ring to rotate.

16. The attachable needle assembly of claim 12, wherein the housing is configured to move from the first position to the second position for each of the plurality of needles.

17. The attachable needle assembly of claim 1, wherein each of the plurality of needles is configured for single use.

18. The attachable needle assembly of claim 1, wherein the follower ring includes two tooth shaped followers and the two tooth shaped followers are circumferentially offset from each other on an internal surface of the follower ring.

19. The attachable needle assembly of claim 1, further comprising
a sealing septum of the needle assembly that seals and maintains a sterile environment for the plurality of needles, wherein
when the housing is in the first position, a distal end of each of the plurality of needles is disposed in the sealing septum of the needle assembly.

20. The attachable needle assembly of claim 1, wherein when the housing is in the second position, a distal end of each of a remaining plurality of needles is disposed in a sealing septum of the needle assembly.

21. The attachable needle assembly of claim 1, wherein when the housing is in the second position, a distal end of the selected needle of the plurality of needles pierces a sealing septum of the needle assembly and is exposed.

22. The attachable needle assembly of claim 1, wherein the plurality of needles includes at least seven needles.

23. The attachable needle assembly of claim 1, wherein the plurality of needles do not pierce the reservoir septum of the medication delivery pen.

24. The attachable needle assembly a claim 1, wherein the plurality of needles only move axially, do not substantially move radially and do not substantially rotate.

25. The attachable needle assembly of claim 1, further including a cap connected to the housing that applies a force to the snap ring when the housing is moving from the second position to the first position.

26. The attachable needle assembly of claim 1, further including
a cover enclosing the needle assembly; and
a label sealing and maintaining sterility of the needle assembly in the cover prior to operating with the medication delivery pen.

27. The attachable needle assembly of claim 1, further including a plurality of indicators that identify a plurality of needle exposure lengths when the housing is moving from the first position to the second position.

28. The attachable needle assembly of claim 27, wherein the plurality of indicators is disposed under the housing and is not visible in the first position.

29. The attachable needle assembly of claim 1, wherein a plurality of needle numbers is sequentially disposed on an outer surface of the snap ring to indicate a number of the plurality of needles available for use.

30. The attachable needle assembly of claim 29, wherein the housing includes a window to displays one of the plurality of needle numbers.

31. The attachable needle assembly of claim 1, wherein the follower ring is in contact with the snap ring.

32. The attachable needle assembly of claim 1, wherein the follower ring moves with the snap ring when the housing moves from the first position to the second position.

33. The attachable needle assembly of claim 1, wherein rotation of the snap ring causes the follower ring to simultaneously rotate.

* * * * *